(12) United States Patent
Garrett et al.

(10) Patent No.: US 11,147,516 B2
(45) Date of Patent: Oct. 19, 2021

(54) METHODS AND SYSTEMS TO QUANTIFY AND REMOVE ASYNCHRONOUS NOISE IN BIOPHYSICAL SIGNALS

(71) Applicant: Analytics For Life inc., Toronto (CA)

(72) Inventors: Michael Garrett, Wilmette, IL (US); Timothy William Fawcett Burton, Toronto (CA); Shyamlal Ramchandani, Kingston (CA); Abhinav Doomra, Toronto (CA)

(73) Assignee: Analytics For Life Inc., Toronto (CA)

( * ) Notice: Subject to any disclaimer, the term of this patent is extended or adjusted under 35 U.S.C. 154(b) by 100 days.

(21) Appl. No.: 16/445,158

(22) Filed: Jun. 18, 2019

(65) Prior Publication Data

US 2019/0384757 A1    Dec. 19, 2019

Related U.S. Application Data

(60) Provisional application No. 62/686,245, filed on Jun. 18, 2018.

(51) Int. Cl.
| | |
|---|---|
| A61B 5/00 | (2006.01) |
| G06F 16/28 | (2019.01) |
| G06K 9/62 | (2006.01) |
| A61B 5/316 | (2021.01) |
| A61B 5/349 | (2021.01) |
| A61B 5/369 | (2021.01) |

(52) U.S. Cl.
CPC ............ *A61B 5/7203* (2013.01); *A61B 5/316* (2021.01); *A61B 5/349* (2021.01); *A61B 5/369* (2021.01); *A61B 5/7267* (2013.01); *G06F 16/285* (2019.01); *G06K 9/6218* (2013.01)

(58) Field of Classification Search
CPC ....... A61B 5/7203; A61B 5/369; A61B 5/349; A61B 5/316; A61B 5/7267; G06F 16/285; G06K 9/6218
See application file for complete search history.

(56) References Cited

U.S. PATENT DOCUMENTS

| | | | |
|---|---|---|---|
| 5,243,993 | A | 9/1993 | Alexander et al. |
| 5,823,957 | A | 10/1998 | Faupel et al. |
| 5,954,660 | A | 9/1999 | Legay et al. |
| 6,014,582 | A | 1/2000 | He |

(Continued)

FOREIGN PATENT DOCUMENTS

| | | |
|---|---|---|
| WO | 2010/061335 | 6/2010 |
| WO | 2012/021307 | 2/2012 |

OTHER PUBLICATIONS

International Search Report and Written Opinion, dated Dec. 4, 2019, received in connection with International Patent Application No. PCT/IB2019/055115.

(Continued)

*Primary Examiner* — Catherine M Voorhees
*Assistant Examiner* — Roland Dinga
(74) *Attorney, Agent, or Firm* — Meunier Carlin & Curfman LLC

(57) ABSTRACT

The exemplified methods and systems described herein facilitate the quantification and/or removal of asynchronous noise, such as muscle artifact noise contamination, to more accurately assess complex nonlinear variabilities in quasi-periodic biophysical-signal systems such as those in acquired cardiac signals, brain signals, etc.

31 Claims, 16 Drawing Sheets

(56) References Cited

U.S. PATENT DOCUMENTS

| | | | |
|---|---|---|---|
| 6,171,256 B1 | 1/2001 | Joo et al. | |
| 8,521,266 B2 | 8/2013 | Narayan et al. | |
| 8,923,958 B2 | 12/2014 | Gupta et al. | |
| 9,144,382 B2 | 9/2015 | Nazarian et al. | |
| 9,289,150 B1 | 3/2016 | Gupta et al. | |
| 9,408,543 B1 | 8/2016 | Gupta et al. | |
| 9,597,021 B1 | 3/2017 | Gupta et al. | |
| 9,655,536 B1 | 5/2017 | Gupta et al. | |
| 9,737,229 B1 | 8/2017 | Gupta et al. | |
| 9,910,964 B2 | 3/2018 | Burton et al. | |
| 9,955,883 B2 | 5/2018 | Gupta et al. | |
| 9,968,265 B2 | 5/2018 | Burton et al. | |
| 9,968,275 B2 | 5/2018 | Gupta et al. | |
| 10,039,468 B2 | 8/2018 | Gupta et al. | |
| 10,292,596 B2 | 5/2019 | Shadforth et al. | |
| 2007/0260151 A1* | 11/2007 | Clifford | A61B 5/7264 600/509 |
| 2009/0299421 A1* | 12/2009 | Sawchuk | A61B 5/7221 607/4 |
| 2013/0096394 A1 | 4/2013 | Gupta et al. | |
| 2013/0303871 A1* | 11/2013 | Kempen | A61B 5/7203 600/372 |
| 2014/0375298 A1 | 12/2014 | Garcia et al. | |
| 2015/0305641 A1* | 10/2015 | Stadler | A61B 5/363 600/510 |
| 2017/0119272 A1 | 5/2017 | Gupta et al. | |
| 2017/0290550 A1* | 10/2017 | Perschbacher | A61B 5/7221 |
| 2018/0000371 A1 | 1/2018 | Gupta et al. | |
| 2018/0249960 A1 | 9/2018 | Gupta et al. | |
| 2018/0325466 A1* | 11/2018 | An | A61B 5/7282 |
| 2019/0117164 A1 | 4/2019 | Gupta et al. | |
| 2019/0200893 A1* | 7/2019 | Grouchy | G06T 11/006 |
| 2019/0214137 A1* | 7/2019 | Gupta | G16H 50/70 |
| 2019/0254531 A1 | 8/2019 | Shadforth et al. | |
| 2019/0365265 A1 | 12/2019 | Grouchy et al. | |

OTHER PUBLICATIONS

Ester, M., et al., "A Density-Based Algorithm for Discovering Clusters in Large Spatial Databases with Noise," Proceedings of the Second International Conference on Knowledge Discover and Data Mining (KDD-96), 1996, pp. 226-231.

Freund, Y., et al., "A Decision-Theoretic Generalization of On-Line Learning and an Application to Boosting," European Conference on Computational Learning Theory, Journal of Computer and System Sciences, vol. 55, 1997, pp. 119-139.

Kohli, S., et al., "Hilbert Transform Based Adaptive ECG R-Peak Detection Technique," International Journal of Electrical and Computer Engineering, vol. 2, No. 52012, pp. 639-643.

Kim, J-H, et al., "Detection of R-Peaks in ECG Signal by Adaptive Linear Neuron (ADALINE), Artificial Neural Network," presented at MATEC Web of Conferences No. 54, 10001, 2016, 4 pages.

Pan, J., et al., "A Real Time QRS Detection Algorithm," IEEE Transactions on Biomedical Engineering, vol. BME-32, No. 3, 1985, pp. 230-236.

International Search Report and Written Opinion, dated Nov. 21, 2016, received in connection with International Patent Application No. PCT/IB2016/055125.

\* cited by examiner

METHODS AND SYSTEMS TO QUANTIFY AND REMOVE ASYNCHRONOUS NOISE IN BIOPHYSICAL SIGNALS

RELATED APPLICATIONS

This application claims to, and the benefit of, U.S. Provisional Appl. No. 62/686,245, filed Jun. 18, 2018, titled "METHODS AND SYSTEMS TO QUANTIFY AND REMOVE ASYNCHRONOUS NOISE IN BIOPHYSICAL SIGNALS," which is incorporated by reference herein in its entirety.

FIELD OF THE INVENTION

The present disclosure generally relates to non-invasive methods and systems for characterizing cardiovascular circulation and other physiological systems. More specifically, in an aspect, the present disclosure relates to the filtering of asynchronous noise from an acquired biophysical signal (e.g., a cardiac signal, a brain signal, etc.). In another aspect, the present disclosure relates to the quality assessment of an acquired signal and the gating of the acquired signal for analysis. In another aspect, the present disclosure relates to normalizing a first set of data sets acquired with a first set of biophysical-signal measurement equipment and normalizing a second set of data sets acquired with a second set of biophysical-signal measurement equipment such that the first set of data sets may be analyzed with the second set of data sets in a machine learning operation.

BACKGROUND

Ischemic heart disease, also known as cardiac ischemia or myocardial ischemia, is a disease or group of diseases characterized by a reduced blood supply to the heart muscle, usually due to coronary artery disease (CAD). CAD typically occurs when the lining inside the coronary arteries that supply blood to the myocardium, or heart muscle, develops atherosclerosis (the hardening or stiffening of the lining and the accumulation of plaque therein, often accompanied by abnormal inflammation). Over time, CAD can also weaken the heart muscle and contribute to, e.g., angina, myocardial infarction (heart attack), heart failure, and arrhythmia. An arrhythmia is an abnormal heart rhythm and can include any change from the normal sequence of electrical conduction of the heart and, in some cases, can lead to cardiac arrest.

The evaluation of CAD can be complex, and many techniques and tools are used to assess the presence and severity of the condition. In the case of electrocardiography, a field of cardiology in which the heart's electrical activity is analyzed to obtain information about its structure and function, significant ischemic heart disease can alter ventricular conduction properties of the myocardium in the perfusion bed downstream of a coronary artery narrowing, or occlusion. This pathology can express itself at different locations of the heart and at different stages of severity, making an accurate diagnosis challenging. Further, the electrical conduction characteristics of the myocardium may vary from person to person, and other factors such as measurement variability associated with the placement of measurement probes and parasitic losses associated with such probes and their related components can also affect the biophysical signals that are captured during electrophysiologic tests of the heart. Further still, when conduction properties of the myocardium are captured as relatively long cardiac phase gradient signals, they may exhibit complex nonlinear variability that cannot be efficiently captured by traditional modeling techniques.

The quantification and filtering of asynchronous noise and artifacts in acquired biophysical signals, e.g., cardiac signals, brain signals, etc., that can facilitate more accurate assessments of pathologies and conditions is desired.

SUMMARY

The exemplified methods and systems described herein facilitate the quantification and/or removal of asynchronous noise, such as skeletal-muscle artifact noise contamination, to more accurately assess complex nonlinear variabilities in quasi-periodic biophysical-signal systems such as those in acquired cardiac signals, brain signals, etc. The exemplified methods and systems described herein further facilitate the assessment of the signal quality of an acquired signal for gating the acquired signal for subsequent analysis.

The term "cardiac signals" (also referred to as heart signals), as used herein, refers to signals associated with the function and/or activity of the electrical conduction system of the heart, e.g., to cause contraction of the myocardium, and includes, in some embodiments, electrocardiographic signals such as those acquired via an electrocardiogram (ECG). The quantification of levels of asynchronous noise such as skeletal-muscle-related-signal contamination and muscle-artifact-noise contamination and other asynchronous-noise contamination in an acquired signal can be subsequently used for the automated rejection of such asynchronous noise from measurements of biophysical signals, such as cardiac signals, to which the presence of such asynchronous noise could have a negative impact to subsequent analyses of the cardiac signals and/or biophysical signals and/or to the clinical prediction/estimation of disease state that assesses for various quasi-periodic features of such quasi-periodic biophysical signal.

The term "brain signals" (also referred to herein as neurological signals), as used herein, refers to signals associated with the brain functions/activities and include, in some embodiments, electroencephalographic signals such as those acquired via an electroencephalogram (EEG). The quantification of levels of asynchronous noise such as extraocular-muscle noise contamination and facial muscle noise contamination and other asynchronous noise contamination in an acquired signal can be subsequently used for the automated or manual rejection of such asynchronous noise from measurements of biophysical signals, such as brain signals, to which the presence of such asynchronous noise could have a negative impact to subsequent analyses of the brain signals and/or biophysical signals and/or to the clinical prediction/estimation of disease state(s) that assess for various quasi-periodic features of such.

For purposes of the present disclosure, the term "biophysical signal" is not meant to be limited to cardiac signals and brain signals but encompasses any mammalian electrical or electrochemical signal capable of being sensed, including without limitation those associated with the central and peripheral nervous systems (e.g., electrical signals from the brain, spinal cord, and/or nerves and their associated neurons), pulmonary, circulatory (e.g., blood), lymphatic, endocrine, digestive, musculoskeletal, urinary, immune, reproductive, integumentary and reproductive systems, as well as electrical signals generated at the cellular level in any place in a mammalian body. While the present disclosure is directed to the beneficial quantification of asynchronous noise in the diagnosis and treatment of cardiac-related pathologies and conditions and/or brain-related pathologies and conditions (including, e.g., coronary arterial disease and pulmonary hypertension (e.g., pulmonary arterial hypertension, pulmonary hypertension due to left heart disease, pulmonary hypertension due to lung disease, pulmonary hypertension due to chronic blood clots, and pulmonary hypertension due to other diseases), as well as other cardiac-related conditions and/or disease and/or brain-related conditions and/or disease mentioned herein), such quantification can be applied to the diagnosis and treatment (including pharmacologic treatment) of any pathologies or conditions in which a biophysical signal is involved in any relevant system of the mammalian body.

Skeletal-muscle-related signals (e.g., as characterized in electromyograms (EMG)) are often characterized as being "in-band noise" with respect to a cardiac signal, a brain signal, etc.—that is, it often occurs in the same or similar frequency range within the acquired biophysical signal. For example, for cardiac signals, the dominant frequency components of signals produced are often between about 0.5 Hz and about 80 Hz. For brain signals, the frequency components are often between about 0.1 Hz and about 50 Hz. Also, depending on the degree of contamination, skeletal-muscle-related signals can also have a same or similar amplitude as typical cardiac-based waveforms and brain-based waveforms, etc. Indeed, the similarity of skeletal-muscle-related signals to cardiac signals, brain signals, etc., can cause significant issues for the automated diagnostic analysis of biophysical signals. Therefore, quantifying the level of skeletal-muscle-related contamination and other asynchronous noise in a measured biophysical signal can be critical for either the quality assessment of acquired biophysical signals and the automated rejection of contaminated acquired signals from being used in subsequent analyses, and/or providing information to the subsequent analyses to enable compensation for the contamination.

A critical observation when quantifying the level of a skeletal-muscle-related signal in an acquired biophysical signal, such as cardiac signal, brain signal, etc., is that skeletal-muscle related signals are not in synchrony with the cardiac signal, brain signal, etc. because the sources of the skeletal-muscle-related signal and the biophysical signals are completely different. For example, cardiac signals are derived from the summation of the action potentials of the cardiac myocytes brain signals are derived from the summation of ionic current within the neurons of the brain, while the skeletal-muscle related signals are derived from the summation of the action potentials of an originating muscle (such as the pectoral muscles, biceps, triceps, etc. Those two sources are unlikely to share a deeper common source that could create synchronicity.

Therefore, skeletal-muscle related signals (and other asynchronous artifacts) can be quantified by comparing, as described herein, acquired biophysical signal(s) and cycles therein to an idealized, representative biophysical signal for that patient to which gross differences between the acquired and idealized biophysical signals can be accounted for as contribution of skeletal-muscle related signals contamination (and other asynchronous signals) in the acquired biophysical signal.

In an aspect, a method is disclosed to filter asynchronous noise (skeletal-muscle artifact noise and other asynchronous noise) from an acquired biophysical-signal data set. The method includes receiving, by a processor, a biophysical-signal data set of a subject; determining, by the processor, at least one template-signal vector data set characteristic of a representative quasi-periodic signal pattern (e.g., a representative heart-beat pattern) of the subject from a plurality of detected quasi-periodic signal cycles detected in the received biophysical-signal data set; applying, by the processor, the at least one determined template-signal vector data set to one or more denoising vector data sets, wherein the one or more denoising vector data sets collectively have a vector length corresponding to a vector length of a portion of the received biophysical-signal data set to be filtered, and wherein the at least one determined template-signal vector data set is i) applied for each of the detected cycles determined to be present in the portion of received cardiac signal data set to be filtered and ii) varied in length to match the vector length of a corresponding detected cycle of the portion of the received biophysical-signal data set to be filtered; and generating a filtered biophysical-signal data set of the biophysical-signal data set, or a portion thereof, by merging the portion of the received biophysical-signal data set to be filtered and the one or more generated denoising vector data sets (e.g., using a window-based operation that applies, in the frequency domain, weighted averages of the received biophysical-signal and the one or more generated denoising vectors).

In some embodiments, the method further includes receiving, by the processor, one or more additional biophysical-signal data sets each contemporaneously acquired from the subject with the biophysical-signal data set; determining, by the processor, at least one template-signal vector data set characteristic of a representative quasi-periodic signal pattern of the subject from a plurality of detected heart-beat cycles detected in each of the received one or more additional biophysical-signal data sets; applying, by the processor, for each of the received one or more additional biophysical-signal data sets, a plurality of determined template-signal vector data sets to one or more denoising vector data sets in a repeating manner, wherein the one or more denoising vector data sets collectively have a vector length corresponding to a vector length of a portion of the received additional biophysical-signal data sets to be filtered, and wherein each of the plurality of determined template-signal vector data sets is i) applied for each of the detected cycles determined to be present in the portion of received additional biophysical-signal data sets to be filtered and ii) varied in length to match the vector length of a corresponding detected cycle of the portion of the received additional biophysical-signal data sets to be filtered; and generating a filtered biophysical-signal data set of the biophysical-signal data set, or a portion thereof, by merging the portion of the received biophysical-signal data set to be filtered and the one or more generated denoising vector data sets (e.g., using a window-based operation that applies, in the frequency domain, weighted averages of the received biophysical-signal data set and the one or more generated denoising vector data sets).

In some embodiments, the step of determining the at least one template-signal vector data set characteristic of the representative quasi-periodic signal pattern comprises: determining, by the processor, a plurality of signal features (e.g., R-peaks for cardiac signals) characteristically distinct in the received biophysical-signal data set or a portion thereof; determining, by the processor, a plurality of cycle regions (e.g., a median R-R interval) (e.g., stored in a M×N matrix in which M is a number of detected cycles, and N is about 40% of the median R-R interval) between each of the plurality of determined signal features; aligning, by the processor, each of the plurality of cycle regions to each other to a same aspect of the plurality of signal features or another set of signal features located in each of the cycle regions (e.g., for cardiac signals, features can include initiation of the Q wave, or the peak of the R wave, or delay estimate by cross correlation); and determining, by the processor, each point of the at least one template-signal vector data set using a mean operation or a median operation performed for each set of points among the plurality of cycle regions.

In some embodiments, the received biophysical-signal data set comprises a cardiac signal data set, and wherein the plurality of signal features are selected from the group consisting of: R-peaks in the received cardiac signal data set or a portion thereof, S-peaks in the received cardiac signal data set or a portion thereof, T-peaks in the received cardiac signal data set or a portion thereof, Q-peaks in the received cardiac signal data set or a portion thereof, and P-peaks in the received cardiac signal data, set or a portion thereof.

In some embodiments, the received biophysical-signal data set comprises a cardiac signal data set, wherein the plurality of signal features correspond to R-peaks in the received cardiac signal data set or a portion thereof.

In some embodiments, the step of determining the at least one template-signal vector data set characteristic of the representative quasi-periodic signal pattern further comprises determining, by the processor, a normalizing parameter (e.g., z-score) derived from each the plurality of cycle regions.

In some embodiments, the step of determining the at least one template-signal vector data set characteristic of the representative quasi-periodic signal pattern further comprises normalizing, by the processor, values, or a parameter derived therefrom (e.g., z-score), of each of the plurality of cycle regions to a pre-defined scale (e.g., between "0" and "1" or between "−1" and "1", or between a standard deviation value greater than 0 and less than 10, etc.).

In some embodiments, the step of determining the at least one template-signal vector data set characteristic of the representative quasi-periodic signal pattern further comprises performing, by the processor, clustering-based analysis (e.g., PCA+DBSCAN) of the plurality of cycle regions to determine the presence of more than one dominant cycle morphologies, wherein a template-signal vector is determined for each determined dominant cycle morphology.

In some embodiments, the plurality of cycle regions comprises cycles that are neighboring one another.

In some embodiments, the cycles that are neighboring one another overlap in part with one another.

In some embodiments, the cycles that are neighboring one another do not overlap to one another.

In some embodiments, the filtered biophysical signal data set is generated by using two or more template-signal vector data sets from two or more groups of cycles of the plurality of cycle regions, wherein the two or more groups of cycles of the plurality of cycle regions are neighboring one another.

In some embodiments, the filtered biophysical-signal data set is generated in near real-time as the biophysical-signal (e.g., cardiac signal, pulmonary signal, brain signal) is acquired.

In some embodiments, the filtered biophysical signal data set is generated following the completed acquisition of the biophysical signal.

In some embodiments, the one or more denoising vector data sets are arranged as a 1-dimensional vector.

In some embodiments, the one or more denoising vector data sets are arranged as an N-dimensional vector, wherein N corresponds to a number of detected cycles determined to be present in the portion of received biophysical-signal data set to be filtered.

In some embodiments, the step of applying the plurality of the determined template-signal vector data sets to one or more denoising vector data sets comprises initializing, by the processor, the one or more denoising vector data set as a 1-dimensional vector having a length corresponding to that of the portion of the received biophysical signal to be filtered; and duplicating, by the processor, the determined template-signal vectors in the 1-dimensional vector so as to align at least a data point associated with a peak (e.g., R-peak or cardiac signals) of the determined template-signal vectors to each peak (e.g., R-peak) determined in the received biophysical signal to be filtered.

In some embodiments, during the duplication step, conflict portions of a currently duplicating template-signal vector data set are assigned average values with respect to corresponding portions of a previously duplicated template-signal vector data set to which the currently duplicating template-signal vector data set has a conflict.

In some embodiments, during the duplication step, empty regions in the 1-dimensional vector between a currently duplicating template-signal vector data set and a previously duplicated template-signal vector data set are stored with values interpolated between a last filled value and a next filled value around the empty region.

In some embodiments, the window-based operation comprises: scaling, by the processor, the portion of the received biophysical-signal data set to be filtered with a plurality of window functions having a pre-defined window length to generate a modified biophysical-signal data set; scaling, by the processor, the one or more generated denoising vector data sets with the plurality of window functions to generate a modified denoising vector data sets; determining, by the processor, an envelope of the modified denoising vector data sets (e.g., by using a low-pass filter); converting, by the processor, via a FFT operation, the envelope of the modified denoising vector data sets and of the portion of the received biophysical-signal data set to be filtered to the frequency domain; performing, by the processor, a weighted average operation of the FFT envelope of the modified denoising vector data sets and of the modified biophysical-signal data set using a static, or a set of dynamic, interpolation coefficients to generate a resulting data set; and converting, by the processor, via an inverse FFT operation, the resulting data set to a time series data set as the filtered biophysical-signal data set of the biophysical signal.

In another aspect, a method is disclosed of normalizing a first set of data sets acquired with a set of first measurement equipment (e.g., by removing asynchronous noise) and a second set of data sets acquired with a second set of measurement equipment (e.g., that is configured to remove certain asynchronous noise) such that the first set of data sets is analyzable with the second set of data sets in a machine learning operation. The method includes receiving, by a processor, a set of biophysical-signal data sets of a subject acquired with a set of first measurement equipment (e.g., each equipment of the set of first measurement equipment has a similar or same noise performance characteristic); determining, by the processor, at least one template-signal vector data set characteristic of a representative quasi-periodic signal pattern of the subject from a plurality of detected quasi-periodic signal cycles detected in the received biophysical-signal data set; applying, by the processor, a plurality of the determined template-signal vector data sets, or a vector selected from the group thereof, to one or more denoising vector data sets, wherein the one or more denoising vector data sets collectively have a vector length corresponding to a vector length of a portion of the received biophysical-signal data set to be filtered, wherein each applied template-signal vector data set is i) applied for each of the detected cycles determined to be present in the portion of received biophysical-signal data set to be filtered and ii) varied in length to match the vector length of a corresponding detected cycle of the portion of the received biophysical-signal data set to be filtered; and generating a filtered biophysical-signal data set associated with the biophysical-signal data set, or a portion thereof, as a normalized data set of the biophysical signal, wherein the filtered biophysical signal is generated by merging the portion of the received biophysical signal to be filtered and the one or more generated denoising vectors (e.g., using a window-based operation that applies, in the frequency domain, weighted averages of the received biophysical signal and the one or more generated denoising vectors), wherein the normalized data set associated with the biophysical signal acquired with the first measurement equipment is analyzable (e.g., with skeletal-muscle-related noise/muscle artifact noise removed) as a machine-learning training data set along with a second data set acquired with a second measured equipment.

In some embodiments, a data set of the received biophysical signal comprises data captured from sensors (e.g., in a smart device or in a handheld medical diagnostic equipment) selected from the group consisting of a 12-lead surface potential sensing electrode system (e.g., electrocardiogram system), an intracardiac electrocardiogram, a Holter electrocardiogram, a 6-lead differential surface potential sensing electrode system, a 3-lead orthogonal surface potential sensing electrode system, and a single lead potential sensing electrode system.

In some embodiments, a data set of the received biophysical signal comprises wide-band cardiac phase gradient cardiac signal data (e.g., having at a sampling frequency above about 1 kHz, e.g., above about 10 kHz, above about 40 kHz, above about 80 kHz, above about 500 KHz) derived from biopotential signals simultaneously captured (e.g., having a skew less than about 100 microseconds) from a plurality of surface electrode placed on surfaces of a body in proximity to a heart.

In another aspect, a method is disclosed of rejecting an acquired signal, the method comprising: receiving, by a processor, a biophysical-signal data set of a subject; comparing, by the processor, the received biophysical-signal data set to at least one template-signal vector data set characteristic of a representative quasi-periodic signal pattern within the biophysical-signal data set; and rejecting, by the processor, the received biophysical-signal data set based on the comparison.

In some embodiments, the step of determining the at least one template-signal vector data set characteristic of the representative quasi-periodic signal pattern comprises: determining, by the processor, a plurality of signal features (e.g., R-peaks for cardiac signals) characteristically distinct in the received biophysical-signal data set or a portion thereof; determining, by the processor, a plurality of cycle regions (e.g., a median R-R interval) (e.g., stored in a M×N matrix in which M is a number of detected cycles, and N is about 40% of the median R-R interval) between each of the plurality of determined signal features; aligning, by the processor, each of the plurality of cycle regions to each other to a same aspect of the plurality of signal features or another set of signal features located in each of the cycle regions (e.g., for cardiac signals, features can include initiation of the Q wave, or the peak of the R wave, or delay estimate by cross correlation); and determining, by the processor, each point of the at least one template-signal vector data set using a mean operation or a median operation performed for each set of points among the plurality of cycle regions.

In some embodiments, the step of determining the at least one template-signal vector data set characteristic of the representative quasi-periodic signal pattern further comprises: performing, by the processor, clustering-based analysis (e.g., PCA+DBSCAN) of the plurality of cycle regions to determine the presence of more than one dominant cycle morphologies, wherein a template-signal vector is determined for each determined dominant cycle morphology.

In some embodiments, the method further includes generating, by the processor, a notification of a failed acquisition of biophysical-signal data set, wherein the notification prompts a subsequent acquisition of the biophysical-signal data set to be performed.

In some embodiments, the method further includes causing, by the processor, transmission of the received biophysical-signal data set over a network to an external analysis system, wherein the analysis system is configured to analyze the received biophysical-signal data for presence, or degree, of a pathology or clinical condition.

In some embodiments, the comparison comprises determining the presence of asynchronous noise present in the acquired biophysical-signal data set having a value or energy over a pre-defined threshold.

In another aspect, a method is disclosed of quantifying asynchronous noise in an acquired biophysical signal. The method includes receiving, by a processor, a biophysical-signal data set of a subject; determining, by the processor, a plurality of signal features (e.g., R-peaks for cardiac signals) characteristically distinct in the received biophysical-signal data set or a portion thereof; determining, by the processor, a plurality of cycle regions (e.g., a median R-R interval) (e.g., stored in a M×N matrix in which M is a number of detected cycles, and N is about 40% of the median R-R interval) between each of the plurality of determined signal features; aligning, by the processor, each of the plurality of cycle regions to each other to a same aspect of the plurality of signal features or another set of signal features located in each of the cycle regions (e.g., for cardiac signals, features can include initiation of the Q wave, or the peak of the R wave, or delay estimate by cross correlation); determining, by the processor, each point of the at least one template-signal vector data set using a mean operation or a median operation performed for each set of points among the plurality of cycle regions; and performing, by the processor, clustering-based analysis (e.g., PCA+DBSCAN) of the plurality of cycle regions to determine presence of more than one dominant cycle morphologies, wherein a template-signal vector is determined for each determined dominant cycle morphology.

In an aspect, a system is disclosed to filter asynchronous noise from an acquired biophysical-signal data set, the system comprising: a processor and a memory having instructions stored thereon, wherein execution of the instructions by the processor cause the processor to receive a biophysical-signal data set of a subject; determine at least one template-signal vector data set characteristic of a representative quasi-periodic signal pattern of the subject from a plurality of detected quasi-periodic cycles detected in the received biophysical-signal data set; apply the at least one determined template-signal vector data set to one or more denoising vector data sets, wherein the one or more denoising vector data sets collectively have a vector length corresponding to a vector length of a portion of the received biophysical-signal data set to be filtered, and wherein the at least one determined template-signal vector data set is i) applied for each of the detected cycles determined to be present in the portion of received cardiac signal data set to be filtered and ii) varied in length to match the vector length of a corresponding detected cycle of the portion of the received biophysical-signal data set to be filtered; and generate a filtered biophysical-signal data set of the biophysical-signal data set, or a portion thereof, by merging the portion of the received biophysical-signal data set to be filtered and the one or more generated denoising vector data sets.

In some embodiments, the instructions when executed by the processor further cause the processor to receive one or more additional biophysical signal data sets each contemporaneously acquired from the subject with the biophysical signal data set; determine at least one template-signal vector data set characteristic of a representative quasi-periodic signal pattern of the subject from a plurality of detected heart-beat cycles detected in each of the received one or more additional biophysical signal data sets; apply for each of the received one or more additional biophysical signal data sets, a plurality of determined template-signal vector data sets to one or more denoising vector data sets in a repeating manner, wherein the one or more denoising vector data sets collectively have a vector length corresponding to a vector length of a portion of the received additional biophysical signal data sets to be filtered, and wherein each of the plurality of determined template-signal vector data sets is i) applied for each of the detected cycles determined to be present in the portion of received additional biophysical signal data sets to be filtered and ii) varied in length to match the vector length of a corresponding detected cycle of the portion of the received additional biophysical signal data sets to be filtered; and generate a filtered biophysical signal data set of the biophysical signal data set, or a portion thereof, by merging the portion of the received biophysical signal data set to be filtered and the one or more generated denoising vector data sets.

In some embodiments, the operation of determining the at least one template-signal vector data set characteristic of the representative quasi-periodic signal pattern comprises determining, by the processor, a plurality of signal features characteristically distinct in the received biophysical signal data set or a portion thereof; determining, by the processor, a plurality of cycle regions between each of the plurality of determined signal features;

aligning, by the processor, each of the plurality of cycle regions to each other to a same aspect of the plurality of signal features or another set of signal features located in each of the cycle regions; and determining, by the processor, each point of the at least one template-signal vector data set using a mean operation or a median operation performed for each set of points among the plurality of cycle regions.

In some embodiments, the received biophysical-signal data set comprises a cardiac signal data set, and wherein the plurality of signal features are selected from the group consisting of: R-peaks in the received cardiac signal data set or a portion thereof, S-peaks in the received cardiac signal data set or a portion thereof, T-peaks in the received cardiac signal data set or a portion thereof, Q-peaks in the received cardiac signal data set or a portion thereof, and P-peaks in the received cardiac signal data set or a portion thereof.

In some embodiments, the received biophysical-signal data set comprises a cardiac signal data set, and wherein the plurality of signal features correspond to R-peaks in the received cardiac signal data set or a portion thereof.

In some embodiments, the operation of determining the at least one template-signal vector data set characteristic of the representative quasi-periodic pattern further comprises determining, by the processor, a normalizing parameter derived from each the plurality of cycle regions.

In some embodiments, the operation of determining the at least one template-signal vector data set characteristic of the representative quasi-periodic signal pattern further comprises normalizing, by the processor, values, or a parameter derived therefrom, of each of the plurality of cycle regions to a pre-defined scale.

In some embodiments, the operation of determining the at least one template-signal vector data set characteristic of the representative quasi-periodic signal pattern further comprises performing, by the processor, clustering-based analysis of the plurality of cycle regions to determine the presence of more than one dominant cycle morphologies, wherein a template-signal vector is determined for each determined dominant cycle morphology.

In some embodiments, the plurality of cycle regions comprises cycles that are neighboring one another.

In some embodiments, the cycles that are neighboring one another overlap in part to one another.

In some embodiments, the cycles that are neighboring one another do not overlap to one another.

In some embodiments, the filtered biophysical signal data set is generated by using two or more template-signal vector data sets from two or more groups of cycles of the plurality of cycle regions, wherein the two or more groups of cycles of the plurality of cycle regions are neighboring one another.

In some embodiments, the filtered biophysical signal data set is generated in near real-time as the biophysical signal is acquired.

In some embodiments, the filtered biophysical-signal data set is generated following the completed acquisition of the biophysical signal.

In some embodiments, the one or more denoising vector data sets are arranged as a 1-dimensional vector.

In some embodiments, the one or more denoising vector data sets are arranged as an N-dimensional vector, wherein N corresponds to a number of detected cycles determined to be present in the portion of received biophysical signal data set to be filtered.

In some embodiments, the operation applying the plurality of the determined template-signal vector data sets to one or more denoising vector data sets comprises initializing, by the processor, the one or more denoising vector data set as a 1-dimensional vector having a length corresponding to that of the portion of the received biophysical signal to be filtered; and duplicating, by the processor, the determined template-signal vectors in the 1-dimensional vector so as to align at least a data point associated with a peak of the determined template-signal vectors to each peak determined in the received biophysical signal to be filtered.

In some embodiments, conflict portions of a currently duplicating template-signal vector data set are assigned, during the duplication step, average values with respect to corresponding portions of a previously duplicated template-signal vector data set to which the currently duplicating template-signal vector data set has a conflict.

In some embodiments, empty regions in the 1-dimensional vector between a currently duplicating template-signal vector data set and a previously duplicated template-signal vector data set are stored, during the duplication step, with values interpolated between a last filled value and a next filled value around the empty region.

In some embodiments, the window-based operation comprises scaling, by the processor, the portion of the received biophysical signal data set to be filtered with a plurality of window functions having a pre-defined window length to generate a modified biophysical signal data set; scaling, by the processor, the one or more generated denoising vector data sets with the plurality of window functions to generate a modified denoising vector data sets; determining, by the processor, an envelope of the modified denoising vector data sets; converting, by the processor, via a FFT operation, the envelope of the modified denoising vector data sets and of the portion of the received biophysical signal data set to be filtered to the frequency domain; performing, by the processor, a weighted average operation of the FFT envelope of the modified denoising vector data sets and of the modified biophysical signal data set using a static, or a set of dynamic, interpolation coefficients to generate a resulting data set; and converting, by the processor, via an inverse FFT operation, the resulting data set to a time series data set as the filtered biophysical signal data set of the biophysical signal.

In another aspect, a system is disclosed of normalizing a first set of data sets acquired with a set of first measurement equipment and a second set of data sets acquired with a second set of measurement equipment such that the first set of data sets is analyzable with the second set of data sets in a machine learning operation, the system includes a processor and a memory having instructions stored thereon, wherein execution of the instructions by the processor cause the processor to receive a set of biophysical-signal data sets of a subject acquired with a set of first measurement equipment; determine at least one template-signal vector data set characteristic of a representative quasi-periodic signal pattern of the subject from a plurality of detected quasi-periodic signal cycles detected in the received biophysical-signal data set; apply a plurality of the determined template-signal vector data sets, or a vector selected from the group thereof, to one or more denoising vector data sets, wherein the one or more denoising vector data sets collectively have a vector length corresponding to a vector length of a portion of the received biophysical signal data set to be filtered, wherein each applied template-signal vector data set is i) applied for each of the detected cycles determined to be present in the portion of received biophysical signal data set to be filtered and ii) varied in length to match the vector length of a corresponding detected cycle of the portion of the received biophysical signal data set to be filtered; and generate a filtered biophysical signal data set associated with the biophysical signal data set, or a portion thereof, as a normalized data set of the biophysical signal, wherein the filtered biophysical signal is generated by merging the portion of the received biophysical signal to be filtered and the one or more generated denoising vectors, wherein the normalized data set associated with the biophysical signal acquired with the first measurement equipment is analyzable as a machine-learning training data set along with a second data set acquired with a second measured equipment.

In some embodiments, the system comprises a sensor device selected from the group consisting of a 12-lead surface potential sensing electrode system, an intracardiac electrocardiogram, a Holter electrocardiogram, a 6-lead differential surface potential sensing electrode system, a 3-lead orthogonal surface potential sensing electrode system, and a single lead potential sensing electrode system.

In some embodiments, the system comprises a sensor device configured to acquire biopotential signals simultaneously captured from a plurality of surface electrodes placed on surfaces of a body in proximity to a heart.

In another aspect, a system is disclosed of rejecting an acquired biophysical signal, the system comprising a processor and a memory having instructions stored thereon, wherein execution of the instructions by the processor cause the processor to receive a biophysical-signal data set of a subject; compare the received biophysical-signal data set to at least one template-signal vector data set characteristic of a representative quasi-periodic pattern within the biophysical-signal data set; and reject the received biophysical-signal data set based on the comparison.

In some embodiments, the operation of determining the at least one template-signal vector data set characteristic of the representative quasi-periodic pattern comprises determining, by the processor, a plurality of signal features characteristically distinct in the received biophysical-signal data set or a portion thereof; determining, by the processor, a plurality of cycle regions between each of the plurality of determined signal features; aligning, by the processor, each of the plurality of cycle regions to each other to a same aspect of the plurality of signal features or another set of signal features located in each of the cycle regions; and determining, by the processor, each point of the at least one template-signal vector data set using a mean operation or a median operation performed for each set of points among the plurality of cycle regions.

In some embodiments, the operation of determining the at least one template-signal vector data set characteristic of the representative quasi-periodic pattern further comprises performing, by the processor, clustering-based analysis of the plurality of cycle regions to determine the presence of more than one dominant cycle morphologies, wherein a template-signal vector is determined for each determined dominant cycle morphology.

In some embodiments, the instructions, when executed by the processor, further cause the processor to generate a notification of a failed acquisition of biophysical-signal data set, wherein the notification prompts a subsequent acquisition of the biophysical-signal data set to be performed.

In some embodiments, the instructions, when executed by the processor, further cause the processor to cause transmission of the received biophysical-signal data set over a network to an external analysis system, wherein the analysis system is configured to analyze the received biophysical-signal data for presence, or degree, of a pathology or clinical condition.

In some embodiments, the comparison comprises the operation of determining the presence of asynchronous noise present in the acquired biophysical-signal data set having a value or energy over a pre-defined threshold.

In another aspect, a system is disclosed that is configured to quantify asynchronous noise in an acquired biophysical signal. The system includes a processor and a memory having instructions stored thereon, wherein execution of the instructions by the processor cause the processor to receive a biophysical-signal data set of a subject; determine a plurality of signal features characteristically distinct in the received biophysical-signal data set or a portion thereof; determine a plurality of cycle regions between each of the plurality of determined signal features; align each of the plurality of cycle regions to each other to a same aspect of the plurality of signal features or another set of signal features located in each of the cycle regions; determine each point of the at least one template-signal vector data set using a mean operation or a median operation performed for each set of points among the plurality of cycle regions; and perform clustering-based analysis of the plurality of cycle regions to determine presence of more than one dominant cycle morphologies, wherein a template-signal vector is determined for each determined dominant cycle morphology.

In another aspect, a system is disclosed comprising: one or more processors; and a memory having instructions stored thereon, wherein execution of the instruction by the one or more processor, cause the one or more processors to perform any one of the above-recited method.

In another aspect, a non-transitory computer readable medium is disclosed, the computer readable medium having instructions stored thereon, wherein execution of the instruction by one or more processors, cause the one or more processors to perform any one of the above-recited method.

BRIEF DESCRIPTION OF THE DRAWINGS

The accompanying drawings, which are incorporated in and constitute a part of this specification, illustrate embodiments and, together with the description, serve to explain the principles of the methods and systems contained herein. The patent or application file contains at least one drawing executed in color. Copies of this patent or patent application publication with color drawing(s) will be provided by the Office upon request and payment of the necessary fee.

Embodiments of the present invention may be better understood from the following detailed description when read in conjunction with the accompanying drawings. The drawings include the following figures.

DETAILED SPECIFICATION

Each and every feature described herein, and each and every combination of two or more of such features is included within the scope of the present invention provided that the features included in such a combination are not mutually inconsistent.

Example System

Figure 1A:
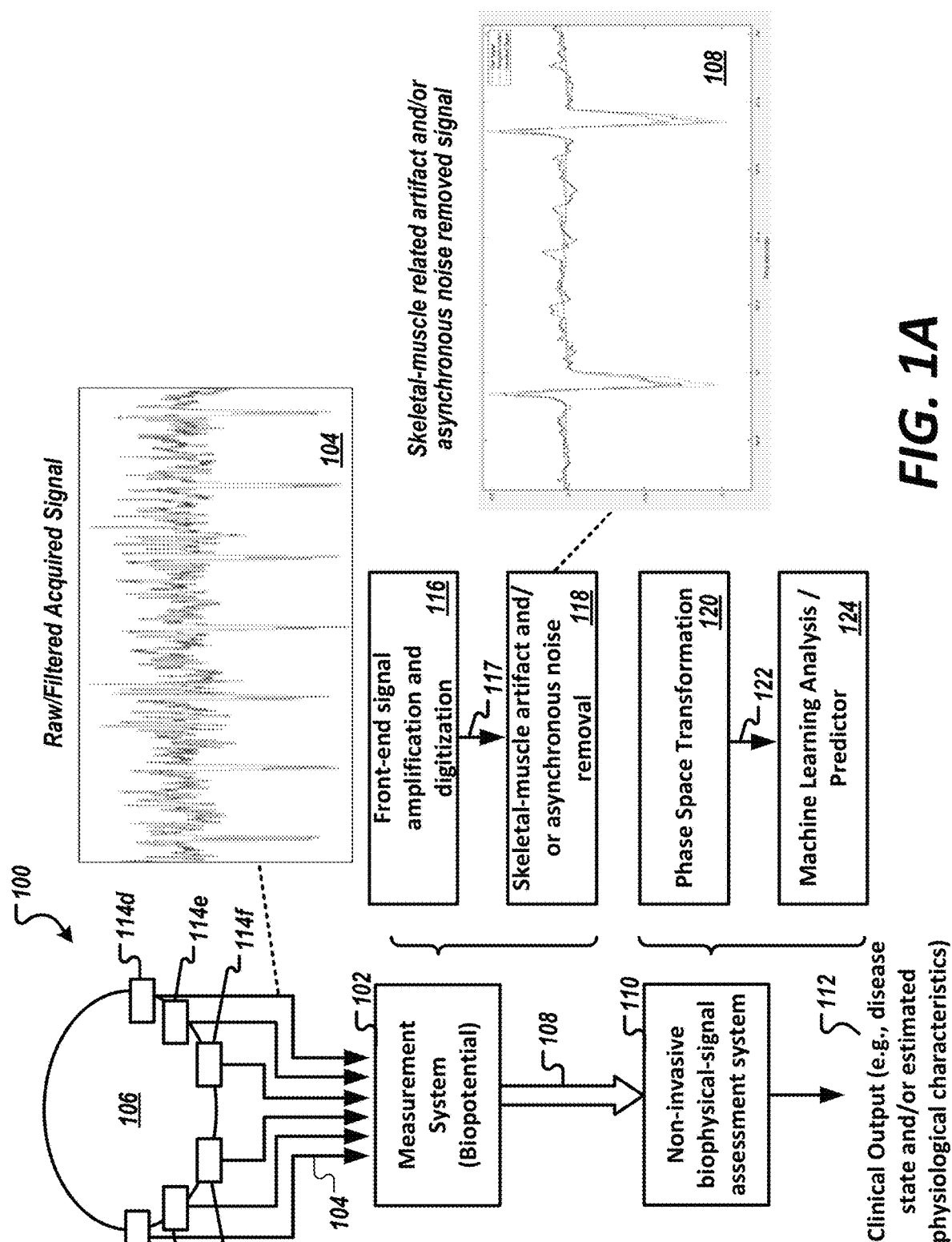
FIG. 1A is a diagram of an example system configured to quantify and remove asynchronous noise and artifact contamination to more accurately assess complex nonlinear variabilities in quasi-periodic systems, in accordance with an illustrative embodiment.

FIG. 1A is a diagram of an example system 100 configured to quantify and remove asynchronous noise such as skeletal-muscle-related artifact noise contamination and to use such quantification to more accurately assess complex nonlinear variabilities in quasi-periodic systems in accordance with an illustrative embodiment. As used herein, the term "remove" refers to any meaningful reduction, in whole or in part, in noise contamination that improves or benefits subsequent analysis.

In FIG. 1A, a non-invasive measurement system 102 acquires a plurality of biophysical signals 104 (e.g., phase gradient biopotential signals) via any number of measurement probes 114 (shown in the system 100 of FIG. 1 as including six such probes 114a, 114b, 114c, 114d, 114e, and 114f) from a subject 106 to produce a phase-gradient biophysical-signal data set 108 that is made available to a non-invasive biophysical-signal assessment system 110 (labeled in FIG. 1 as a "non-invasive biophysical-signal assessment system" 110) to determine a clinical output 112. In some embodiments, the clinical output includes an assessment of the presence or non-presence of a disease and/or an estimated physiological characteristic of the physiological system under study.

In some embodiments, and as shown in FIG. 1A, the system 102 is configured to remove asynchronous noise contamination (e.g., via process 118) from the acquired biophysical-signal data set 117 generated by a front-end amplification and digitization operation 116. The removal operation 118 is based on a quantification of the asynchronous noise potentially present in the acquired signal 114. The process 118 of removing asynchronous noise could be performed in near real-time once a representative cycle data set is established, e.g., from a few samples of the acquired data set. In some embodiments, a few hundred samples can be used to establish representative cycle data set. In other embodiments, a few thousand samples can be used to establish a representative cycle data set.

The measurement system 102, in some embodiments, includes a biopotential-based measurement system configured to acquire wide-band biopotential biophysical signals. In the electrocardiography context, the measurement system 102 is configured to capture cardiac-related biopotential or electrophysiological signals of a mammalian subject (such as a human) as wide-band cardiac phase gradient signals. An example of the measurement system 102 is described in U.S. Publication No. 2017/0119272 and in U.S. patent application Ser. No. 15/248,838, each of which is incorporated by reference herein in its entirety.

In some embodiments, the wide-band biopotential biophysical signals are captured as unfiltered mammalian electrophysiological signals such that the spectral component(s) of the signals are not altered. Indeed, the wide-band biopotential biophysical signals are captured, converted, and even analyzed without having been filtered (via, e.g., hardware circuitry and/or digital signal processing techniques, etc.) (e.g., prior to digitization) that otherwise can affect the phase linearity of the biophysical signal of interest. In some embodiments, the wide-band biopotential biophysical signals are captured in microvolt or sub-microvolt resolutions that are at, or significantly below, the noise floor of conventional electrocardiographic and other biophysical-signal acquisition instruments. In some embodiments, the wide-band biopotential biophysical signals are simultaneously sampled having a temporal skew or "lag" of less than about 1 microseconds, and in other embodiments, having a temporal skew or lag of not more than about 10 femtoseconds. Notably, the exemplified system minimizes non-linear distortions (e.g., those that can be introduced via certain filters) in the acquired wide-band phase gradient signal to not affect the information therein.

As noted above, the measurement system 102 may be used to capture other mammalian biopotential or electrophysiological signals, such as, e.g., cerebral/neurological biopotential signals or other mammalian biopotential signals associated with various biological systems as described elsewhere herein.

Referring still to FIG. 1A, the assessment system 110 is configured to receive the acquired biophysical-signal data set 108 (e.g., denoised, in some embodiments) (e.g., over a network) and to generate, via a transformation operation 120 (labeled as "phase space transformation" 120), one or more three-dimensional vectorcardiogram data sets 122 for analysis, via, e.g., machine learning operation and/or a predictor operation (shown as step 124), of the phase-gradient biophysical-signal data set 108. Examples of the transformation operation and machine learning/predictor operation is discussed below as well as in U.S. Publication No. 2013/0096394, which is incorporated by reference herein in its entirety.

Figure 1B:
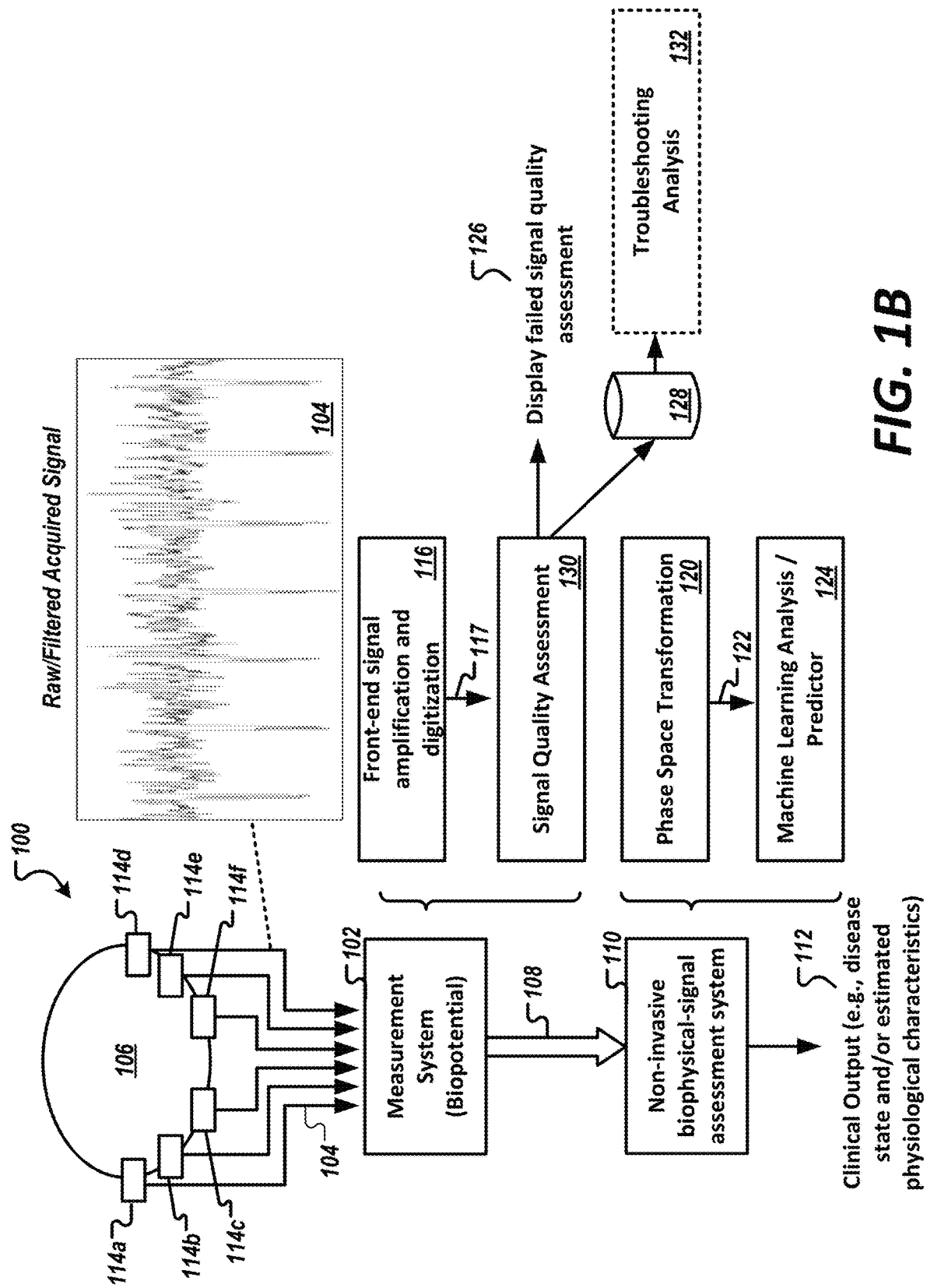
FIG. 1B is a diagram of an example system configured to reject an acquired biophysical signal based on a quantification of asynchronous noise and artifact contamination, in accordance with another illustrative embodiment.

In some embodiments, the measurement system 102 is configured to assess the signal quality of the acquired biophysical signal and to reject the acquired signal data set based on such assessment. FIG. 1B is a diagram of an example system configured to reject an acquired biophysical signal based on a quantification of asynchronous noise and artifact contamination, in accordance with another illustrative embodiment. In some embodiments, the measurement system 102 is configured to perform the asynchronous noise removal operation 118 and the signal quality assessment operation 130 based on the quantification of the asynchronous noise.

Because the clinical analysis of the acquired biophysical signal 108 is performed, in some embodiments, on a separate system (e.g., by the assessment system 110) from the measurement system 102, a signal quality check ensures that the acquired biophysical-signal data set 108 is suitable for subsequent clinical analysis. The near real-time operation may facilitate the prompting of the re-acquisition of the biophysical-signal data set by the non-invasive measurement system 102, thus, ensuring that the acquired biophysical-signal data set is not contaminated by asynchronous noise (such as skeletal-muscle-related noise) prior to the biophysical-signal data set being subjected, or made available, to further processing and analysis for a clinical assessment.

In some embodiments, the signal quality assessment operation is performed in near real-time, e.g., less than about 1 minute or less than about 5 minutes, to which the system can prompt for the re-acquisition of the biophysical signal data set. The near real-time assessment allows the re-acquisition of the biophysical-signal data set prior to the patient leaving the testing room where the test is conducted.

In some embodiments, the non-invasive measurement system 102 is configured to generate a notification 126 (labeled in FIG. 1B as "Display failed signal quality assessment" 126) of a failed or unsuitable acquisition of biophysical-signal data set, wherein the notification prompts that the re-acquisition of another set of the biophysical-signal data set. The notification may be a visual output, an audio output, or a tactile output that is provided to a technician in proximity to the patient.

In some embodiments, the rejected biophysical-signal data set may be stored (128) for further troubleshooting analysis (132) of defects that led to the rejection of the acquired signal. To this end, the rejected biophysical-signal data set is not used in subsequent analysis (e.g., 120, 124) to yield the clinical output 112.

Figure 1C:
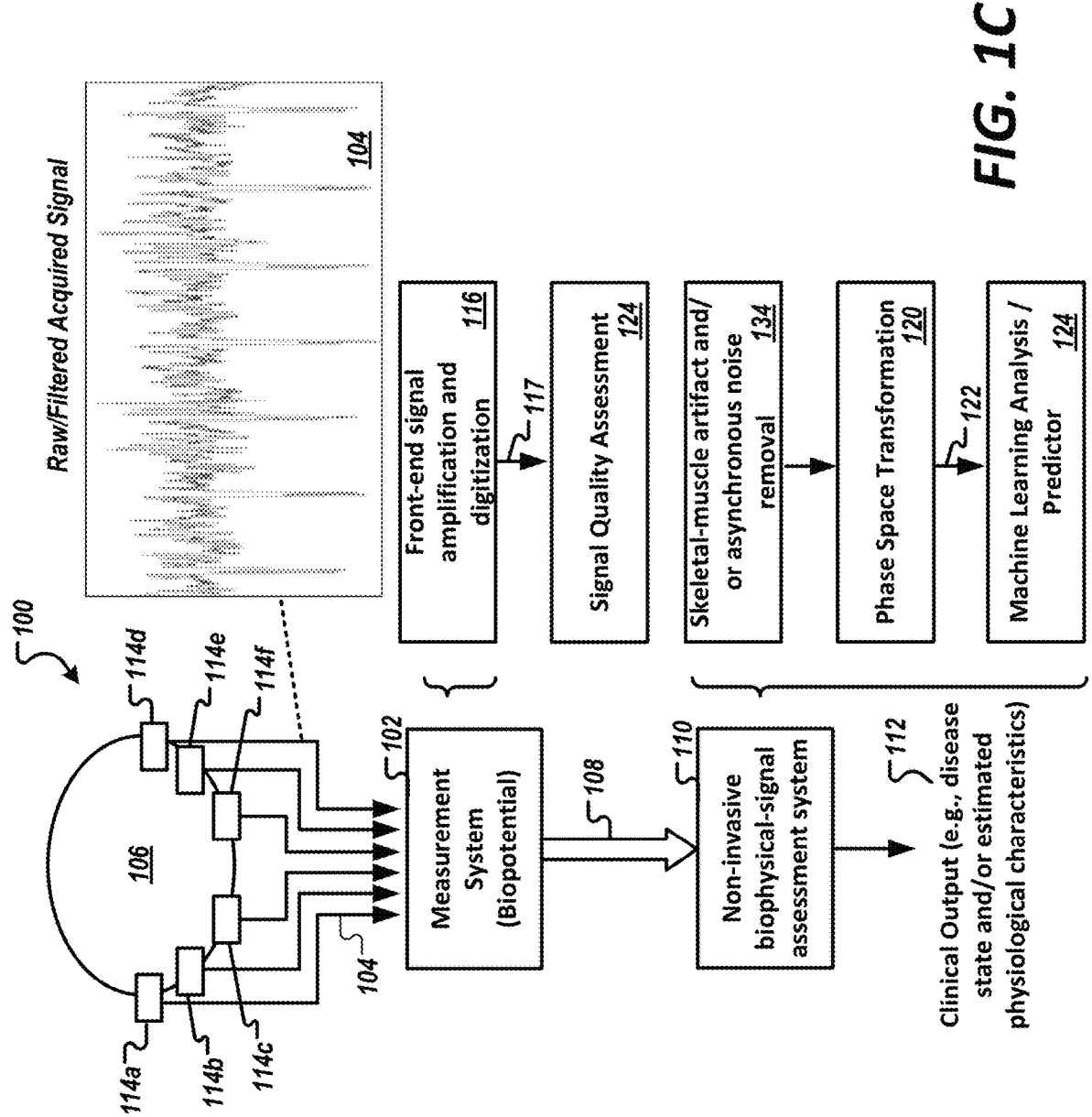
FIG. 1C is a diagram of an example system configured to remove asynchronous noise and/or reject an acquired biophysical signal, in accordance with another illustrative embodiment.

FIG. 1C is a diagram of an example system 100 configured to quantify asynchronous noise such as skeletal-muscle-related artifact noise contamination and using such quantification to remove such contamination and/or reject an acquired biophysical signal, in accordance with another illustrative embodiment. In FIG. 1C, the assessment system 110 is shown configured to further pre-process (134) the received biophysical-signal data set 108 by rejecting the received biophysical-signal data set and/or removing the asynchronous noise from the received biophysical-signal data set. The pre-processing operation 132 may be performed as a substitute to, or as an additional quality operation of, the asynchronous noise removal operation 118 (as performed on the measurement system 102) and/or the signal-quality assessment operation 130 (as performed on the measurement system 102).

Asynchronous Noise Removal

Figure 2:
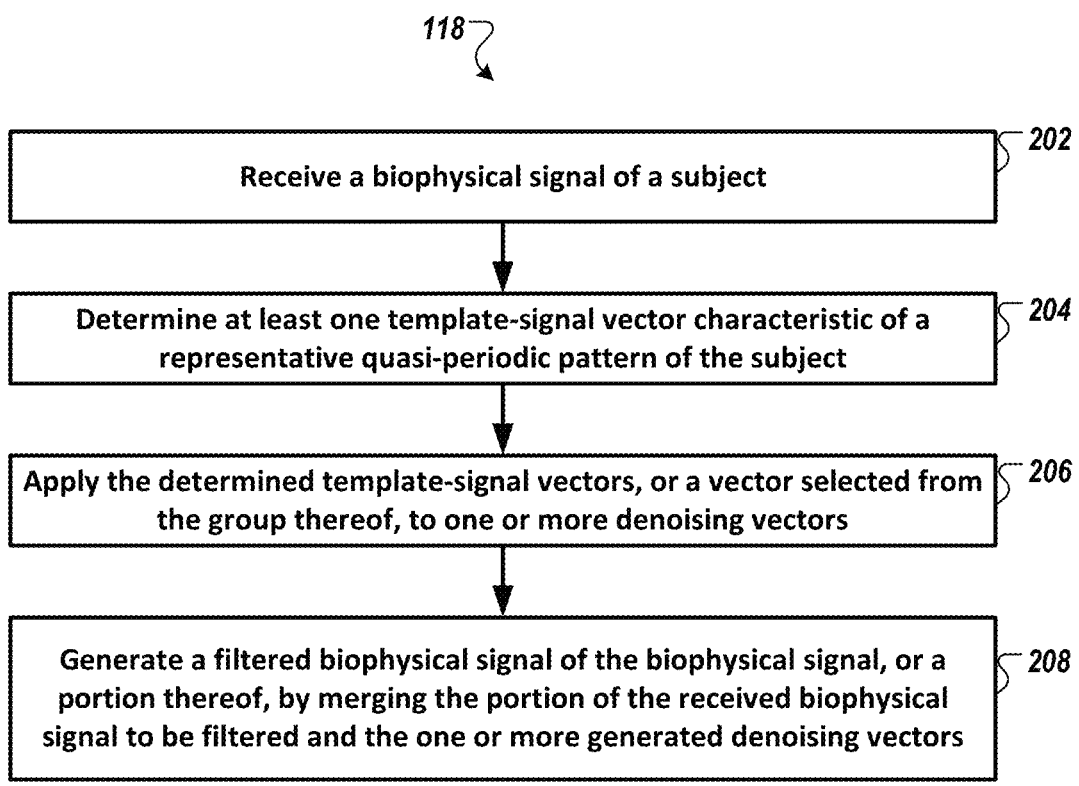
FIG. 2 shows an exemplary method of removing asynchronous noise from an acquired biophysical signal (e.g., acquired cardiac signal, acquired brain signal, etc.) in accordance with an illustrative embodiment.

FIG. 2 shows an exemplary method 118 of removing asynchronous noise from an acquired biophysical signal in accordance with an illustrative embodiment. As shown in FIG. 2, the method 118 includes the step of receiving (step 202), by a processor, a biophysical-signal data set (e.g., data set 108) of a subject 106. As noted above, the removal operation 118 can be performed by the measurement system 102 and/or the assessment system 110. For cardiac signals, a hand-held or other devices may be used to collect a patient's resting thoracic physiologic signals, e.g., from a set of six probes or electrodes (e.g., probes 114a-114f), arranged along three orthogonal axes corresponding to the X, Y, and Z channels. The electrodes as part of the non-invasive measurement system 102 can acquire the phase-gradient biophysical-signal data set 108 without the use of ionizing radiation, contrast agents, exercise, or pharmacologic stressors. The non-invasive measurement system 102, in some embodiments, samples at about 8 kHz for a duration of between about 30 and about 1400 seconds, preferably for about 210 seconds. The acquired data points are transferred as part of the data set 108 to the assessment system 110 and evaluated by an analytic engine therein employing machine-learned algorithms/predictors.

Other conventional electrode sets and electrographic acquisition methodologies may be used to which the method and system disclosed herein can be applied.

Referring still to FIG. 2, the method 118 further includes determining (step 204), by a processor, at least one template-signal vector data set (also referred to as a "representative vector data set") characteristic of a representative heart-beat pattern of the subject from a plurality of detected heart-beat cycles detected in the received cardiac signal data set (e.g., set 108).

Referring still to FIG. 2, the method 118 further includes applying, by a processor, the determined template-signal vector data set to one or more denoising vector data sets. In some embodiments, the template-signal vector data set is applied for each of the detected cycles determined to be present in the portion of the received biophysical-signal data set (e.g., data set 108) to be filtered. In some embodiments, the template-signal vector data set is varied in length to match the vector length of a corresponding detected cycle of the portion of the received biophysical-signal data set (e.g., data set 108) to be filtered. The denoising vector data sets collectively have a vector length corresponding to a vector length of a portion of the received biophysical-signal data set (e.g., data set 108) to be filtered.

Referring still to FIG. 2, the method 118 further includes generating (step 208), by a processor, a filtered biophysical-signal data set (also referred to as a denoised signal data set) of the acquired biophysical signal, or a portion thereof, by merging the portion of the received biophysical-signal data set (e.g., data set 108) corresponding to the portion to the signal to be filtered and the one or more generated denoising vector data sets. In some embodiments, the merging operation is performed using a window-based operation that applies, in the frequency domain, weighted averages of the received biophysical-signal data set (e.g., data set 108) and the one or more generated denoising vector data sets.

In other embodiments, the merging operation is performed in the time domain.

Figure 3:
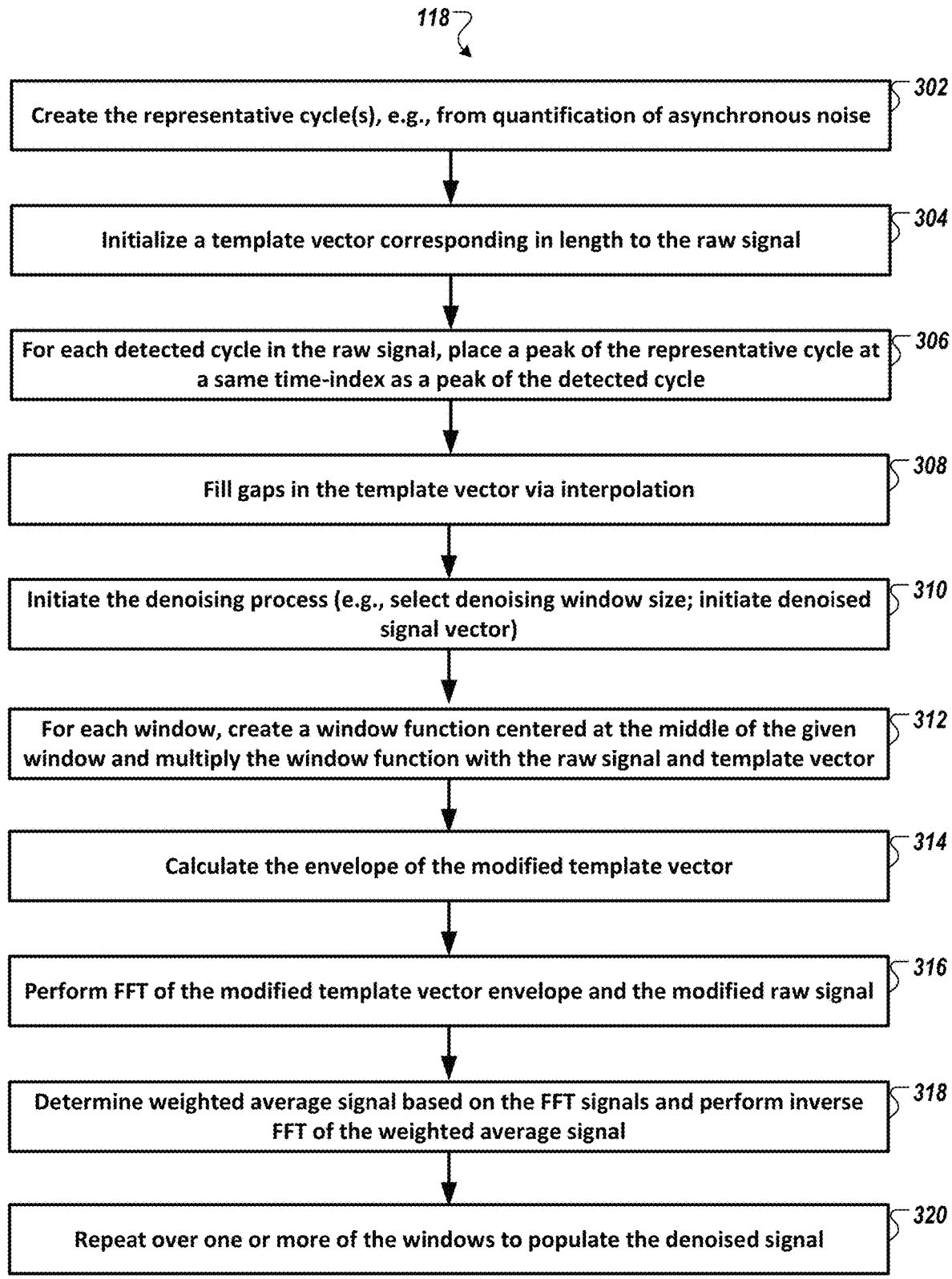
FIG. 3 is a diagram showing an example implementation method of the process of FIG. 2, in accordance with an illustrative embodiment.
Figure 4:
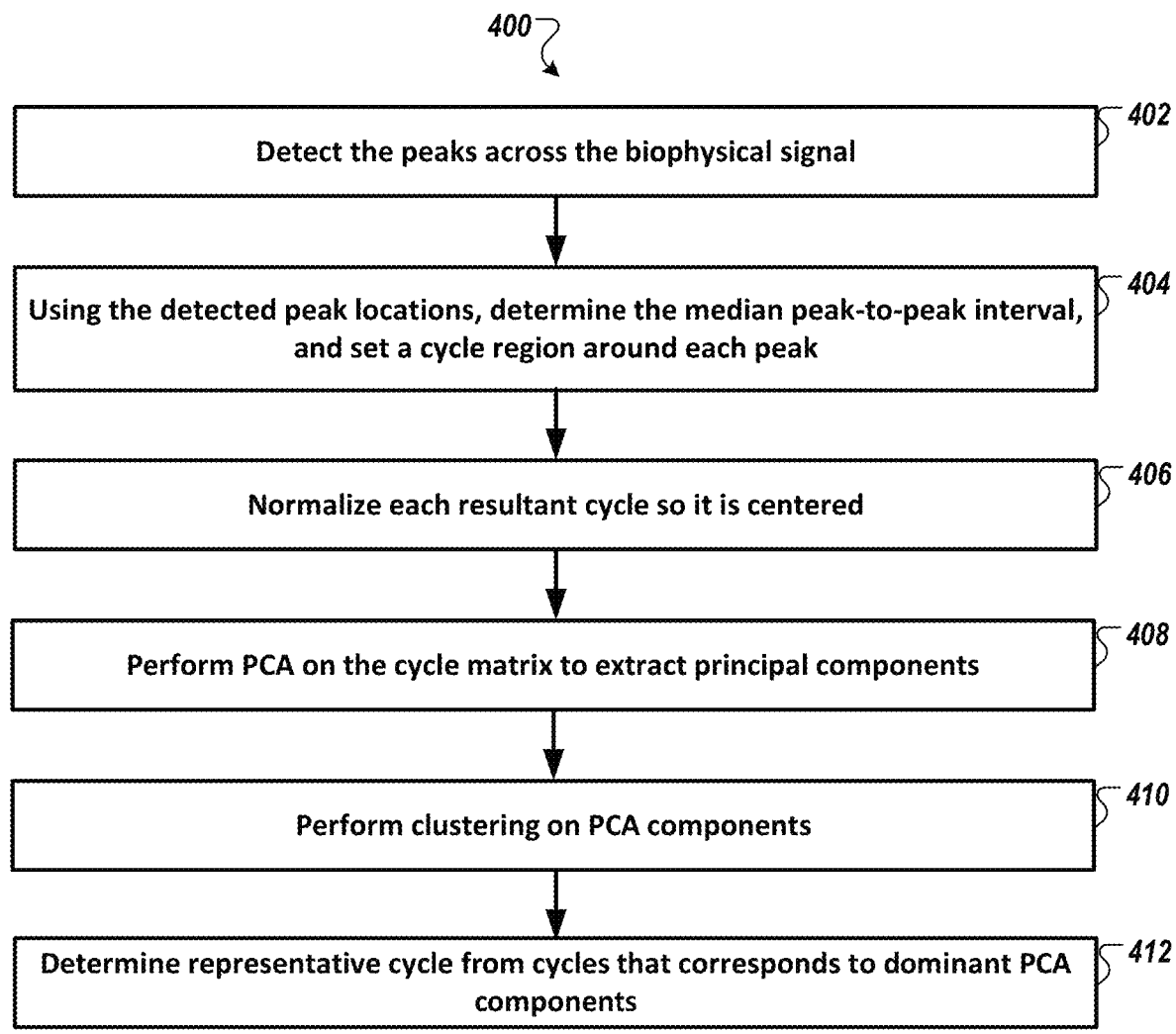
FIG. 4 is a flow diagram of an example method of representative cycle data set in accordance with an illustrative embodiment.
Figure 6:
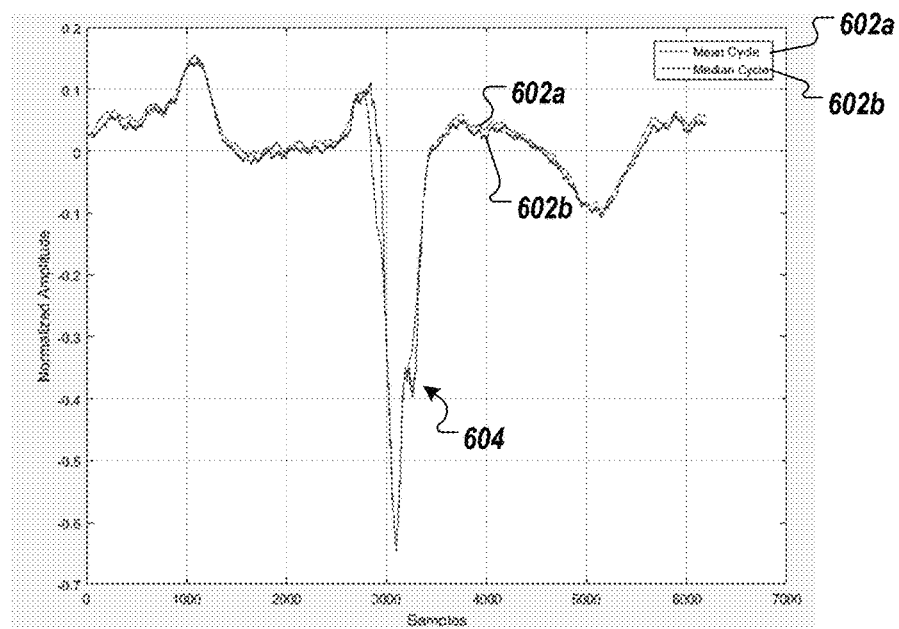
FIG. 6 is a diagram of a representative cycle data set characteristic of a representative quasi-periodic signal pattern (e.g., representative heart-beat pattern in an acquired cardiac signal), in accordance with an illustrative embodiment.

FIG. 3 is a diagram showing an example implementation method 118 of the process of FIG. 2 in accordance with an illustrative embodiment. Method 118 includes creating (step 302), by a processor, one or more representative cycle data set(s) each characteristic of a representative quasi-periodic signal pattern of the subject from a plurality of detected quasi-periodic signal cycles detected in the received biophysical signal(s) (or dataset associated therewith). For cardiac signals, the representative quasi-periodic signal pattern can be characterized as a representative heart-beat pattern. The term quasi-periodic, as used herein, generally refers to a characteristic of a signal system that cycles with, at a minimum, two frequency components, of which the ratio is not a rational number. The representative cycle data set is also referred to herein as the template-signal vector data set. FIG. 4 is a flow diagram of an example method of representative cycle data set in accordance with an illustrative embodiment. FIG. 6 is a diagram of a representative cycle data set 602 (shown as 602a, 602b) characteristic of a representative quasi-periodic pattern (e.g., representative heart-beat pattern in an acquired cardiac signal). Discussion of FIG. 4 and FIG. 6 is provided in subsequent sections.

Referring still to FIG. 3, step 304 to step 312 describe an example to apply, by a processor, the template-signal vector data set (e.g., representative cycle data set) to the one or more denoising vector data sets (e.g., a template-signal vector data set) to generate a denoised signal data set. As shown in FIG. 3, step 304 includes initializing a "template vector" data set that has a length corresponding to that of the input raw signal data set. That is, the length of the initialized template vector data set is the same as the length of the input raw signal data set. For example, a raw signal data set acquired over a 210-second period at 8 kHz yields via step 304 a template vector data set having a length of 1,680,000 samples for each acquired data channel.

Step 306 includes populating, by a processor, the template vector data set with the representative vector data set(s). That is, in some embodiments, for each detected cycle in the raw signal data set, method 118 includes placing or duplicating the representative vector data set 602 in the template vector data set. Each of the representative vector data set 602 is placed such that a determined peak (e.g., R-peak) of the representative vector data set 602 is aligned to a same, or similar, time-index as a corresponding peak (e.g., R-peak) of each detected cycle.

Figure 7:
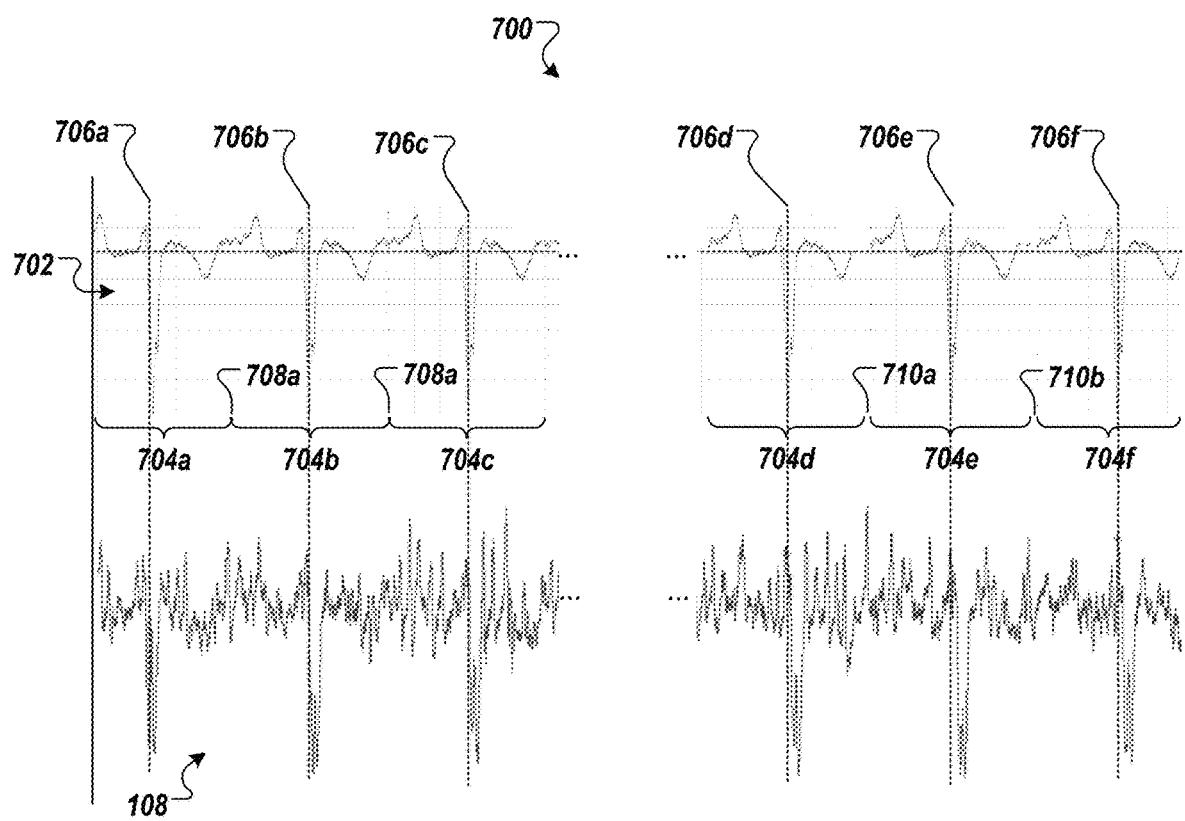
FIG. 7 shows a diagram of a method to generate the template-vector data set (e.g., in an acquired cardiac signal) in accordance with an illustrative embodiment.

FIG. 7 shows a diagram 700 of a method to generate, by a processor, the template-vector data set in accordance with an illustrative embodiment. In FIG. 7, diagram 700 includes i) a plot of the template vector data set 702 populated with the representative vector data set 602 (shown as 704a, 704b, 704c, 704d, 704e, and 704f) and ii) a plot of the received biophysical-signal data set (e.g., data set 108), for a given measurement channel, with detected cycles identified therein. As shown in FIG. 7, the representative vector data sets (e.g., 704a-704f) are placed/reproduced in the template vector data set 702 such that peaks (e.g., maximum peaks corresponding to R-peaks in an acquired cardiac signal with each peak shown as 706a-706f) of the representative vector data sets (e.g., 704a-704f) are aligned to peaks of the biophysical-signal data set 108.

It is possible that more than one representative vector data sets may exist, with each corresponding to an assessed quasi-periodic signal pattern (e.g., a heat-beat pattern for cardiac signals). When there are more than one representative cycle data sets, then method 118, in some embodiments, further includes placing a representative cycle data set selected to correspond (i.e., more closely matches) to a given current cycle in the raw signal data set.

Referring still to FIG. 7, when placing or reproducing the representative cycle data set 602 in the template vector data set 702, if the representative cycle data set being placed conflicts with existing data in the template vector data set, then the overlapping portion (shown as 708a, 708b in FIG. 7) of the existing data samples and the overlapping portion of the new data samples are averaged. If there are gaps (e.g., shown as 710a, 710b) in the template vector data set 702, then the gaps (e.g., 710a, 710b) may be filled, by a processor, in the template vector data set with data values determined, e.g., an optional interpolation operation (e.g., between the last filled value and the next filled value around the empty region), shown in FIG. 3 as step 308.

Once the template vector data set 702 has been created, method 118 includes initiating (step 310 in FIG. 3), by a processor, a denoising process. Step 310, in some embodiments, includes selecting a window size of windows over which the denoising operation is performed and a value for an interpolation coefficient to control the influence of the template vector data set against the raw signal data set.

In some embodiments, each window has a window size of about 0.25 seconds. In other embodiments, a window size less than about 0.25 seconds is used. In yet other embodiments, a window size greater than about 0.25 seconds is used.

In some embodiments, a static value for the interpolation coefficient is about 0.75 (that is, the influence attributed to the template vector data set is about three times that of the raw signal data set). In other embodiments, the interpolation coefficient has a value less than about 0.75. In yet other embodiments, the interpolation coefficient has a value greater than about 0.75. The values of the interpolation coefficient and the window size can be assessed based on the need to eliminate the noise versus that to maintain signal variability. In some embodiments, the window size or the interpolation coefficients are allowed to vary dynamically, e.g., based on an assessment of the signal, e.g., change with respect to an automatically quantified level of contamination (e.g., skeletal-muscle related contamination) in the signal.

Referring still to FIG. 3, step 310 includes initializing a blank/null vector data set that will eventually become the denoised signal data set 114. The initialized denoised signal vector data set, in some embodiments, has the same number of samples as the raw signal data set 114 of interest, that is, a same number of samples of the raw signal 114 to be used in the subsequent machine learning analysis.

Referring still to FIG. 3, step 312 includes creating, by a processor, a window function for each of the windows over which to perform the denoising operation. In some embodiments, for each window, step 312 includes creating a Hamming window data set centered at a middle portion of the window. When the Hamming window data set is not placed at the exact middle sample of the signal data set, then the Hamming window data set is placed in asymmetric relation to the full signal data set so that samples that are equal distances away from the middle of the windows have an equal value in the Hamming window data set. The window function enhances, in some embodiments, the ability of the FFT operation to extract spectral data from signals by reducing the effects of leakage that may occur during an FFT operation of the data. Put any way, the window function can attenuate or remove high-frequency components that result from discontinuities in the discretization of the data and the analysis using window functions. Other types of window function may be applied, including, e.g., Hann window, Blackman window, Harris window, sine window, Nuttall window, triangular window, and combinations thereof, among others. Step 312 further includes multiplying each of the raw signal data set 108 and the populated template vector data set 702 against the window function to generate a modified raw signal data set and a modified template vector data set.

Referring still to FIG. 3, method 118 includes calculating (step 314), by a processor, an envelope of the modified template vector data set by performing a low-pass filtering operation on the data set. In some embodiments, a Butterworth filter is used. In some embodiments, the Butterworth filter is a 5th order filter with a normalized cut-off frequency of 0.025. In some embodiments, a Chebyshev filter is used.

Step 316 includes performing, by a processor, a Fast Fourier Transform (e.g., discrete FFT) of each of the modified template vector envelope data set and the modified raw signal data set to transform each of them into the frequency domain.

Step 318 includes merging, by a processor, the modified template vector envelope data set and the modified raw signal data set in the frequency domain. In some embodiments, a weighted average operation of the modified template vector envelope data set and the modified raw signal data set in the frequency domain is performed. In some embodiments, the weights used in the interpolation are the interpolation coefficients that were initially set to control the influence of the template vector against the raw signal.

Step 320 includes performing, by a processor, an inverse Fourier Transform operation to transform the resultant data back to the time domain. The resultant data is assigned as a current window of the denoised signal data set. The process is repeated for all the windows, or a portion thereof, to populate the remaining portion of the denoised signal data set.

Figure 8:
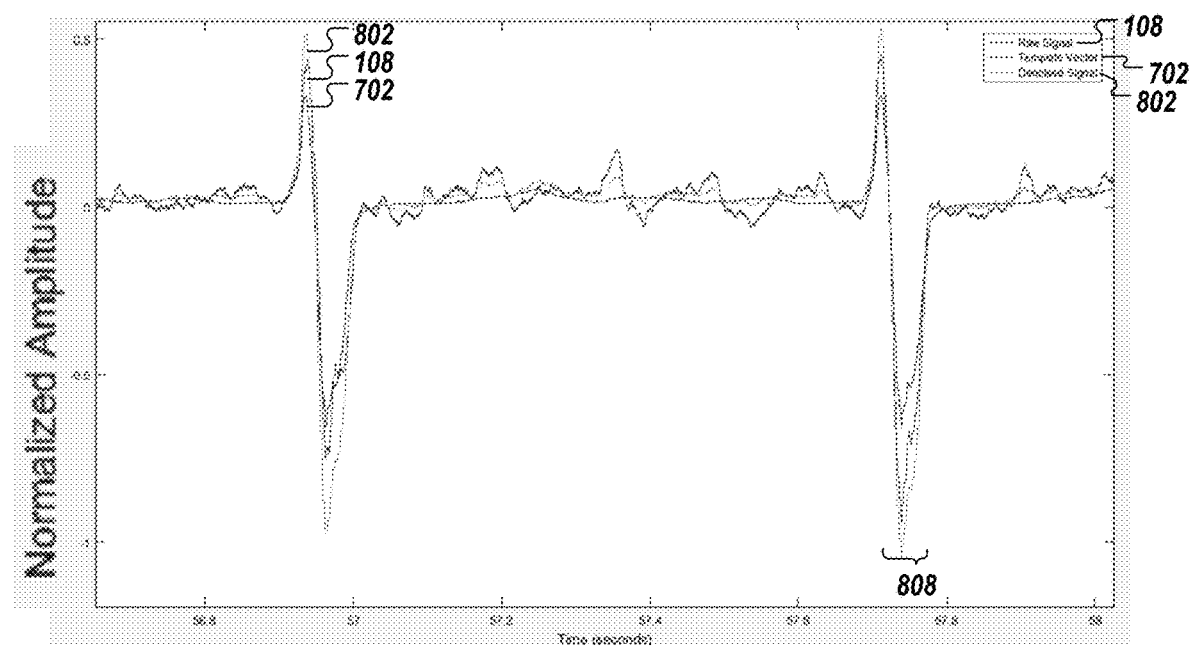
FIG. 8 is an example plot of the raw biophysical-signal data set, a generated biophysical template-vector data set, and a resulting denoised, biophysical-signal data set, in accordance with an illustrative embodiment.

FIG. 8 is an example plot of the raw biophysical-signal data set 108 (e.g., shown as "Raw Signal" 108), a generated template-vector data set 702 (e.g., shown as "Template Vector" 702), and a resulting denoised signal data set 802 (e.g., shown as "Denoised Signal").

As shown in FIG. 8, the raw signal data set 108 is heavily contaminated with noise (e.g., skeletal-muscle-related noise). Application of the template vector data set 702 completely removes, in some embodiments, that noise while maintaining some of the high-frequency information in the QRS waveform (e.g., shown at the notching 808 that occurs at around time index 57.8 seconds), but template vector data set 702 does not contain most of the variability (i.e., cardiac signal variability) present in the raw signal data set. The denoised signal data set 802 includes such variability (i.e., cardiac signal variability) information as in the raw signal data set 108.

Indeed, methods described herein involve generating a filtered cardiac signal (namely, the denoised signal) of the cardiac signal, or a portion thereof, by merging the portion of the received biophysical signal to be filtered (e.g., as the modified raw signal) and the one or more generated denoising vectors (e.g., as the modified template vector envelope).

Determination of a Representative Cycle of a Quasi-Periodic Signal Pattern

As noted above, FIG. 4 is a diagram of a method 400 to determine a template-signal vector data set of a representative cycle of a quasi-periodic signal pattern (e.g., a representative cycle of a heartbeat pattern). Method 400 may be part of an assessment or quantification of skeletal-muscle-related artifact and noise contamination in a biophysical signal (e.g., cardiac signal, brain signal, etc.).

As shown in FIG. 4, the method 400 includes, first, detecting (step 402), by a processor, peaks (e.g., R-peaks corresponding to maximum depolarization for a cardiac signal) across the biophysical-signal data set (e.g., data set 108), or a portion thereof. In some embodiments, the peaks are detected using a Pan-Tompkins algorithm, e.g., as described in Pan & Tompkins, A Real Time QRS Detection Algorithm, IEEE Transactions on Biomedical Engineering, Volume 32-3, 230-236, 1985, which is incorporated by reference herein in its entirety. In other embodiments, other algorithms to detect peaks in the cardiac signal data set can be used. Examples include those described in Makwana et al. "Hilbert transform based adaptive ECG R-peak detection technique," International Journal of Electrical and Computer Engineering, 2(5), 639 (2012); Lee et al., "Smart ECG Monitoring Patch with Built-in R-Peak Detection for Long-Term HRV Analysis," Annals of Biomedical Engineering. 44(7), 2292-3201 (2016); and Kim et al., "Detection of R-Peaks in ECG Signal by Adaptive Linear Neuron (ADA-LINE)," Artificial Neural Network, presented at MATEC Web of Conferences, 54, 10001 (2016), each of which is incorporated by reference herein in its entirety.

In some embodiments, the system is configured to assess the number of cycles and boundaries of the cycles in the biophysical-signal data set (e.g., data set 108) to which subsets of the cycles in determined groups of neighboring cycles are subsequently used to determine template-signal vector data sets of representative cycles. In some embodiments, the system is configured to assess the boundaries of the cycles in the entire biophysical-signal data set or the portion desired to be analyzed. In other embodiments, the system is configured to assess the boundaries of the cycles for a pre-defined number of neighboring cycles in the portion of the biophysical-signal data set (e.g., data set 108) of interest.

Neighborhood/neighboring cycles may be defined as, in some embodiments, as ±1, 2, . . . 10 cycles around a middle cycle of a set of determined cycles. In other embodiments, the neighborhood/neighboring cycles may be defined as, +1, 2, . . . 20 cycles with respect to a beginning cycle of a set of determined cycles. In other embodiments, the neighborhood/neighboring cycles may be defined as −1, 2, . . . 20 cycles with respect to a last cycle of a set of determined cycles.

To this end, multiple template-signal vector data sets may be generated to which each template-signal vector data set is respectively applied to the cycles used to generate it. For example, where neighborhood group 1 is composed of cycles 1 . . . 10 and derives template vector #1, analysis of cycles 1-10 (e.g., as discussed herein) are evaluated against only template vector #1; where neighborhood group 2 is composed of cycles 5 . . . 15 (e.g., having some and derives template vector #2), analysis of cycles 5-10 (e.g., as discussed herein) are evaluated against template vector #1 and template vector #2 (e.g., by an average of vector #1 and #2); where neighborhood group 3 is composed of cycles 10 . . . 20 (e.g., having some and derives template vector #2), analysis of cycles 10-15 (e.g., as discussed herein) are evaluated against template vector #2 and template vector #3 (e.g., by an average of vector #2 and #3).

Indeed, in some embodiments, the analysis is performed until all cardiac cycles (e.g., 3.5-minute PSR recording×60 BPM=210), or portions of the biophysical-signal data set of interest have been evaluated.

This neighborhood approach may reduce sensitivity to long-term variation by only incorporating local cycles into the template, though it may also reduce robustness to noise because fewer component cycles are used or analyzed. Indeed, using the full recording may capture natural cardiac variation in the entire data set but may also create non-noise-based deviations between the template and the test cardiac cycles. By using all of the signals in neighborhoods, but in neighboring groups, all of the signals (and inherent variation in the acquired signal) are still assessed, and sensitivity is locally improved.

The number of neighborhood sizes maybe 10, e.g., as discussed above, or it may be a user-defined parameter. In some embodiments, the neighborhood size is determined based on some assessed variation in the signals. Indeed, the number of neighborhood sizes maybe 2, 3, 4, 5, 6, 7, 8, 9, 10. In some embodiments, the number of neighborhood sizes may be greater than 10, e.g., between 10 or 15. In some embodiments, the number of neighborhood sizes may be greater than 15, e.g., between 15-25. In some embodiments, the number of neighborhood sizes may be greater than 25, e.g., between 25-50.

In some embodiments, the neighborhood or groupings of cycles are defined by an offset size. In some embodiments, the offset size is the distance in the index count from a reference point in one cycle to the next cycle. The reference point may be a middle point, a beginning point, or an ending point in the cycle. In the example above, where cycles are defined from 1 . . . 10, 5 . . . 15, 10 . . . 20, etc., the offset size is 5 (per the reference point being at the beginning, middle, or end).

In some embodiments, depending on the offset size and neighborhood size, each given cycle may have one or more template-signal vector data sets compared to it to determine a metric (e.g., mean, median, mode, among others as discussed herein) for that template-signal vector data set. Then the metric can be combined to provide a revised score for that template-signal vector data set.

For example, a template-signal vector data set may be defined as preceding and tailing neighboring points of a reference point defined in the middle of a given defined cycle. The template-signal vector data set can be generated (e.g., based on mean, mode, median, etc.) based only on the preceding and trailing neighboring points (and not on the reference point defined in the middle of the cycle). Once the template-signal vector data set is generated, the template-signal vector data set is compared to the middle of a given defined cycle to determine a score for that score.

In some embodiments, the analysis can be iterative, where the score for subsequent cycles is combined. For example, in cycle #1, a score #1 is determined for cycle #2. Then, for cycle #2, a score #2 is determined based on a local score determined from only cycle #2 and then having that local score combined with the score from cycle #1. Then, for cycle #3, a score #3 is determined based on a local score determined from only cycle #3 and then having that local score combined with the score from cycles #1 and #2. This iterative analysis can be applied for all or portion of the input data set of interest.

Indeed, the system may choose to only apply the template to the single cycle at, e.g., the exact center of the neighborhood. As discussed, every single cycle is then assessed against a single template, and that single template is unique across all the possible templates. This type of analysis provides different vantages of viewing the local effects of the cycles.

Figure 9:
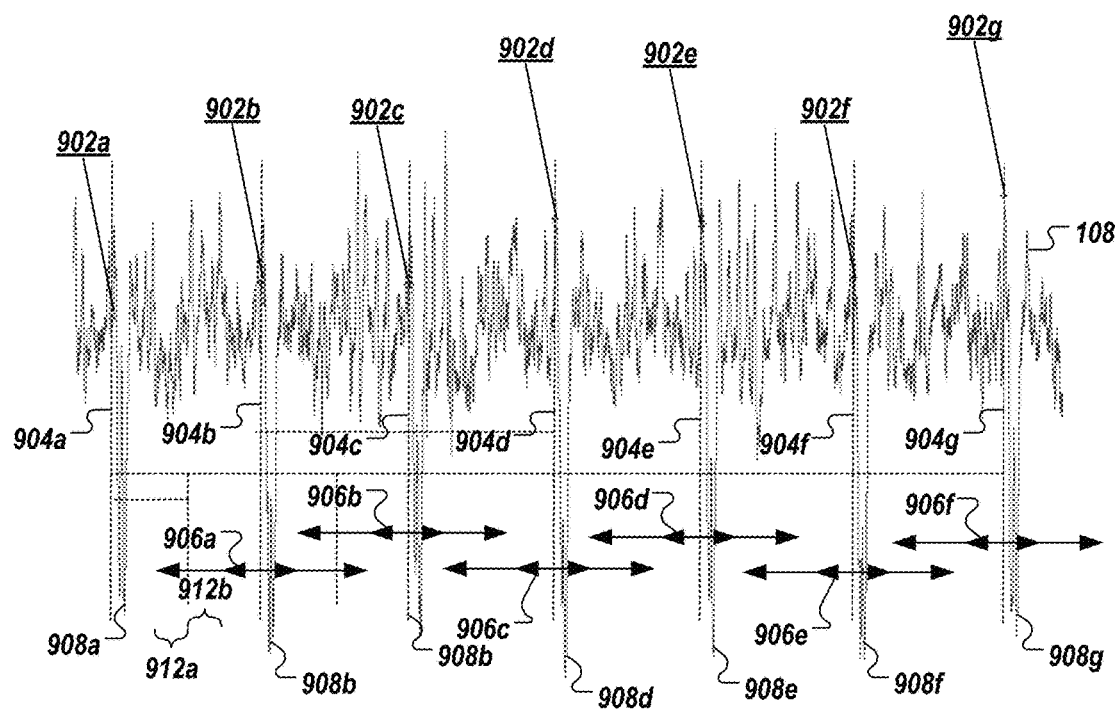
FIG. 9 shows a diagram of a process to segment biophysical cycles (e.g., cardiac cycles) from the biophysical-signal data set (e.g., cardiac signal data set) to quantify asynchronous noise contamination in the biophysical-signal data set, in accordance with an illustrative embodiment.

Method 400 includes using (step 404), by a processor, the detected peak locations to determine a median peak-to-peak interval (e.g., median R-R peak for a cardiac signal) and to set a cycle region around each peak (e.g., R-peak for a cardiac signal). For cardiac signals, the cycle region is set around the R-peak and includes both the P wave and the completion of the T wave. FIG. 9 shows a diagram of a process for a processor to segment biophysical-signal cycles from the biophysical-signal data set to quantify skeletal-muscle-related noise contamination in the biophysical-signal data set. As shown in FIG. 9, the detected peak locations (e.g., shown as 902a-902g) is used to determine a median peak-to-peak interval (e.g., median R-R peaks for cardiac signals as shown with 904a-904g) and to set a cycle region (e.g., shown as 906a-906f) around each peak (e.g., R-peaks for cardiac signals as shown with 908a-908g). FIG. 9 further shows that the cycle region is set around the R-peak and includes both the P wave (e.g., shown as 910a-910g) and completion of the T wave (e.g., shown as 912a-912g) for a cardiac signal. In some embodiments, the ranges are from about −20% to about +20% of the median interval (e.g., shown as 912a, 912b). Each of the cycle regions (e.g., 906a-906f) can be stored by a processor in a matrix (also referred to as a "cycle matrix). The cycle matrix may be M×N in which M is the number of detected cycles, and N is 40% of the median peak-to-peak interval (e.g., median R-R intervals for cardiac signals) in which the 40% of the peak-to-peak interval represents the full temporal "width" of the cycle. Specifically, once the median peak-to-peak interval (e.g., median R-R interval for cardiac signals) is known across the dataset, the signal can be divided in half, e.g., to get the "20%" that reaches both forward and backward in time from the peak (e.g., R-peak) to capture the other waves (e.g., T wave and P wave for a cardiac signal). Of course, other cycle region lengths can be used for cardiac signals and for the various distinct waves in brain signals, etc.

Figure 10A:
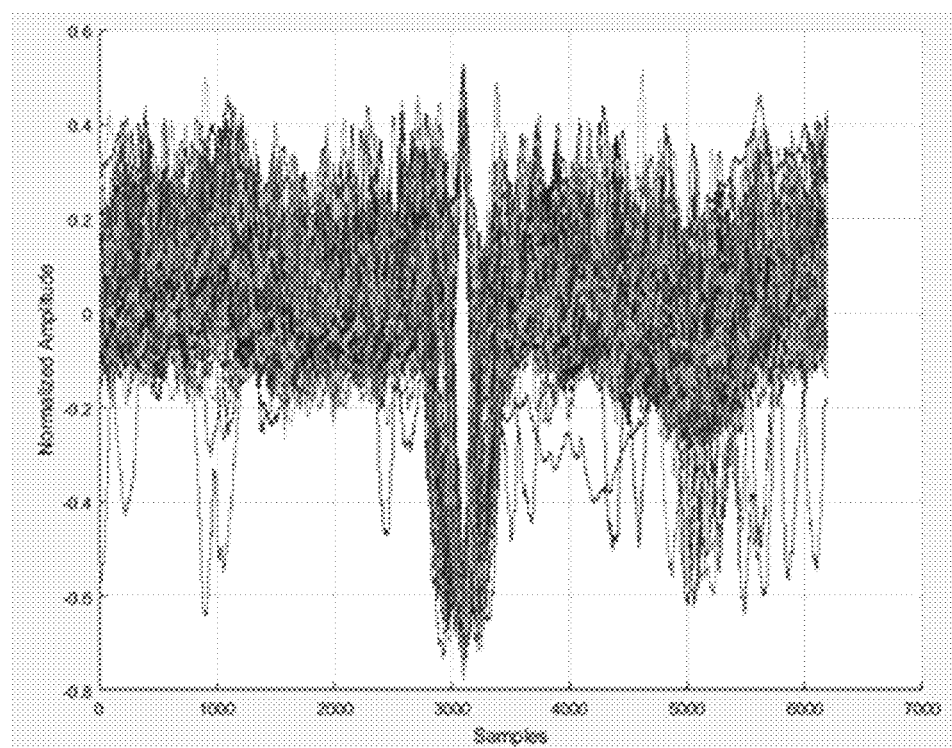
FIG. 10A shows a plot of results of the normalization process of FIG. 4 in accordance with an illustrative embodiment.

Referring to FIG. 4, method 400 includes normalizing (step 406), by a processor, each cycle to remove any offset. FIG. 10A shows a plot of results of the normalization process of FIG. 4 in accordance with an illustrative embodiment. In FIG. 10A, each cycle region (e.g., 906a-906f) of the biophysical-signal data set (e.g., data set 108) is normalized by a processor to remove any offsets such that the average value of each cycle region is zero. The normalized cardiac signal data set, as shown, can have a range of "1" and "−1", though that range can vary depending on the distribution of the data.

In some embodiments, the centering operation includes the operation of time-aligning the same feature (e.g., peaks) among the waveforms. Examples of these features include, for cardiac signals, an initiation of the Q wave, a peak of the R wave, or a delay estimate determined by a cross-correlation operation, among others. In some embodiments, the amplitude normalization operation uses features of the QRS waveform as a basis to determine the gain term (e.g., a short average may be taken just prior to the QRS).

In other embodiments, each cycle is normalized according to z-scores. Z-score value for a given data point in the template signal vector data set can be calculated as a difference between the value of the given data point and a mean of a set of cycles in which the difference is then normalized by the standard deviation of that given data point to the same indexed data value of the set of cycles. In some embodiments, the z-score may be outputted as a cycle variability score. Cycle variability may refer to the degree of variability between cycles in an acquired biophysical data set that may be attributed to asynchronous noise, among others.

Figure 11:
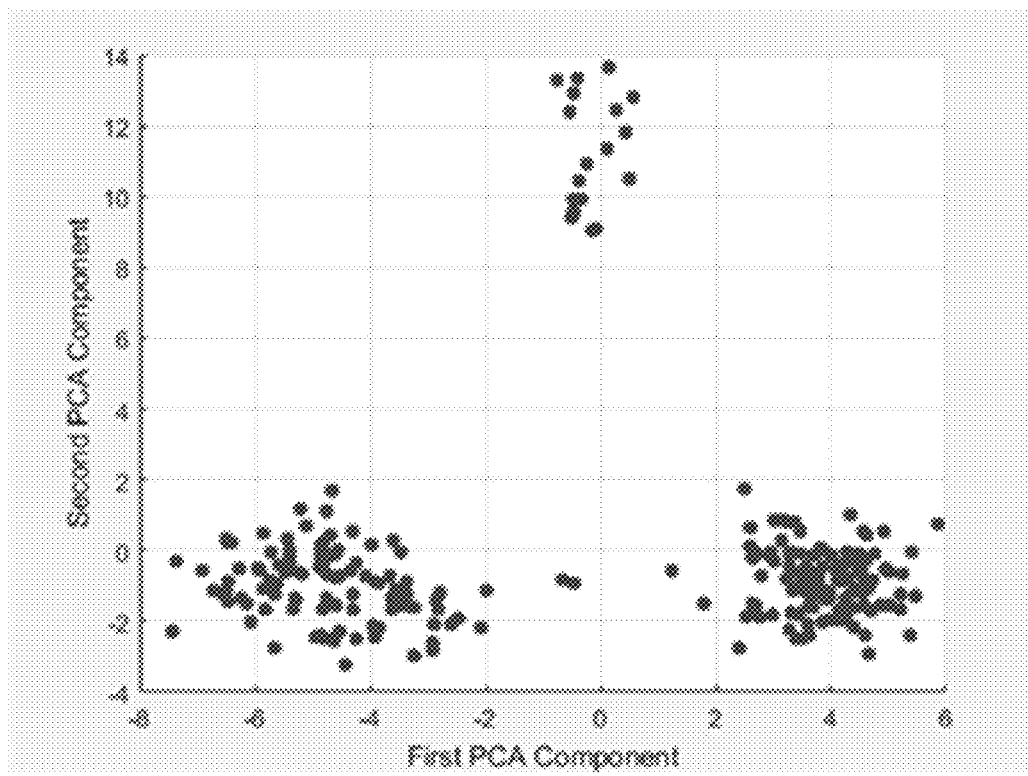
FIG. 11 shows an example output of a principal component analysis of a generated cycle matrix, in accordance with an illustrative embodiment.

Referring still to FIG. 4, method 400 further includes performing, by a processor, a principal component analysis (PCA) on the generated cycle matrix to extract the first two principal components. FIG. 11 shows an example output of a principal component analysis operation performed on the generated cycle matrix.

Referring still to FIG. 4, method 400 further includes performing (step 410), by a processor, a clustering operation on the output of the principal component analysis. An example of a clustering operation that can be used includes the DBSCAN algorithm as described in Ester, Kriegel, Sander, Xu, "A density-based algorithm for discovering clustering in large spatial databases with noise," Proceedings of the Second International Conference on Knowledge Discover and Data Mining. Pages 226-231, which is incorporated by reference herein in its entirety. In some embodiments, the clustering operation is configured to be performed on the first two PCA components, which, in some embodiments, represent the cycles in a two-dimensional space. If the algorithm detects a second dominant cluster representing more than 10% of the total number of cycles, then that signifies the presence of a second dominant cycle morphology, such as premature ventricular contractions. It is noted that FIG. 11 does not contain multiple distinct cycle morphologies, per its identification by DBSCAN. The data set visually appears to have two levels due to the level of EMG in the signal.

Referring still to FIG. 4, method 400 includes extracting (step 412), by a processor, a representative cycle based on all, or some of, the cycles that correspond to the dominant PCA cluster; e.g., as detected by DBSCAN. The representative cycle may be extracted in one or several ways, each with different characteristics. In some embodiments, each of the data points in the representative cycle will embody an underlying distribution, where that distribution is composed of that time-point in all the M cycles. For example, taking the mean (across all M points, for each N) has a low-pass filtering effect (removing both high-frequency information and noise), while taking the median preserves high-frequency information in a non-linear fashion. The differing impact of the compression technique, mean vs. median, is accounted for by varying underlying distributions. If the M points are normally distributed, then the mean and median have the same result but start to differ with more complex distributions, such as those with non-zero skewness, and especially in combination with negative kurtosis or in the presence of multimodality.

As noted above, FIG. 6 shows an example mean representative cycle (e.g., 602a) and median representative cycle (e.g., 602b) for the same underlying cycles. It is observed that the fragmentation (e.g., a high-frequency content that is preserved in the median cycle, but removed in the mean cycle, e.g., as shown at arrow 604) is preserved in the median cycle between 3000-3500 samples, while the mean cycle has removed that feature (604). Additionally, some high-frequency noise is visible in the median beat, but not the mean beat, throughout the representative cycle. Using the median operation preserves high-frequency features that may not be present in the mean representation due to changes in QRS morphology over time or because of time smearing associated with beat detection alignment. In addition, functions to describe distributions may be used; such functions would create spectral masks that can remove or enhance characteristics that are desired for removal or preservation (such as, for example, the mode of the kernel density estimate of the underlying distribution).

Put another way, the mean beat can be used to generate a "cleaner" representation of the cycle (i.e., less high-frequency content, where that high-frequency content includes both signal and noise characteristics), whereas the median beat contains that high-frequency content. Either one of these approaches may be more desired depending on the situation. For example, the median beat may be used when i) it is desired to ensure that the high-frequency component of the biophysical signal characteristics is captured and maintained for analysis even if there are some high-frequency noise present that could cloud the analysis or ii) there is little or low high-frequency noise in the signal.

The process of FIG. 4 of determining a representative cycle of a quasi-periodic signal cycle can be a part of a large study to quantify skeletal-muscle-related noise and other asynchronous noise contamination in an acquired biophysical signal.

Figure 10B:
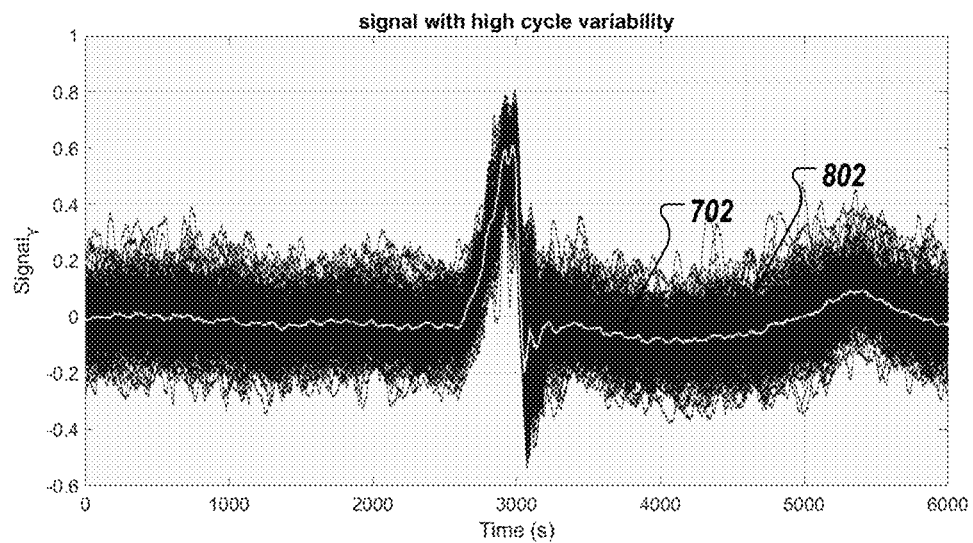
FIG. 10B shows a template-signal vector data set superimposed on top of a set of stacked cycles for a high-noise signal.
Figure 10C:
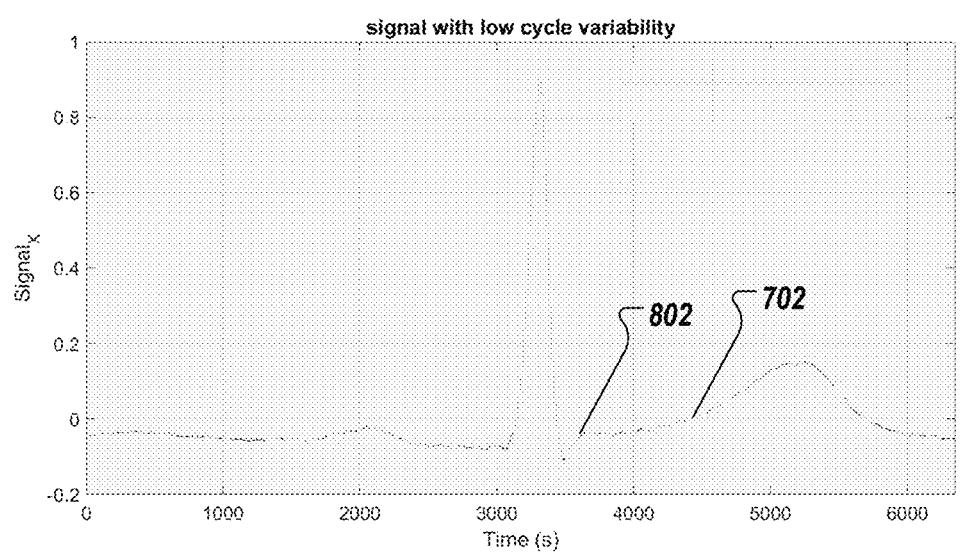
FIG. 10C shows a template-signal vector data set superimposed on top of a set of stacked cycles for a low-noise signal.

In some embodiments, portions of the resulting windows that are neighbors within a set of windows are combined and assessed (e.g., to generate the template signal or to reject a signal). FIG. 10B shows a template-signal vector data set superimposed on top of a set of stacked cycles for a high-noise signal. FIG. 10C shows a template-signal vector data set superimposed on top of a set of stacked cycles for a low-noise signal. FIG. 10A is based on a single PSR recording, and FIG. 10B is based on a second single PSR recording.

Once is cycle is identified (e.g., in each of these cases), the identified cycles can be stacked (i.e., plotted or arranged on top of each other). For example, cycle 1 data point 1 is placed at x=1, and cycle 1 data point 6000 is placed at x=6000; then cycle 150 (for example) data point 1 is also placed at x=1, and cycle 150 data point 6000 is also placed at x=6000.

In FIGS. 10B and 10C, once the data are stacked, a template-signal vector data set 702 corresponding to a template for a given cycle can be generated.

Notably, FIGS. 10B and 10C demonstrate intermediate outputs of an embodiment. FIG. 10B shows that this technique is capable of extracting a meaningful template vector in the presence of very high noise (where the typical cycle isn't otherwise visually obvious), while FIG. 10C shows that the technique is able to extract the typical cycle under ideal conditions.

Figure 5:
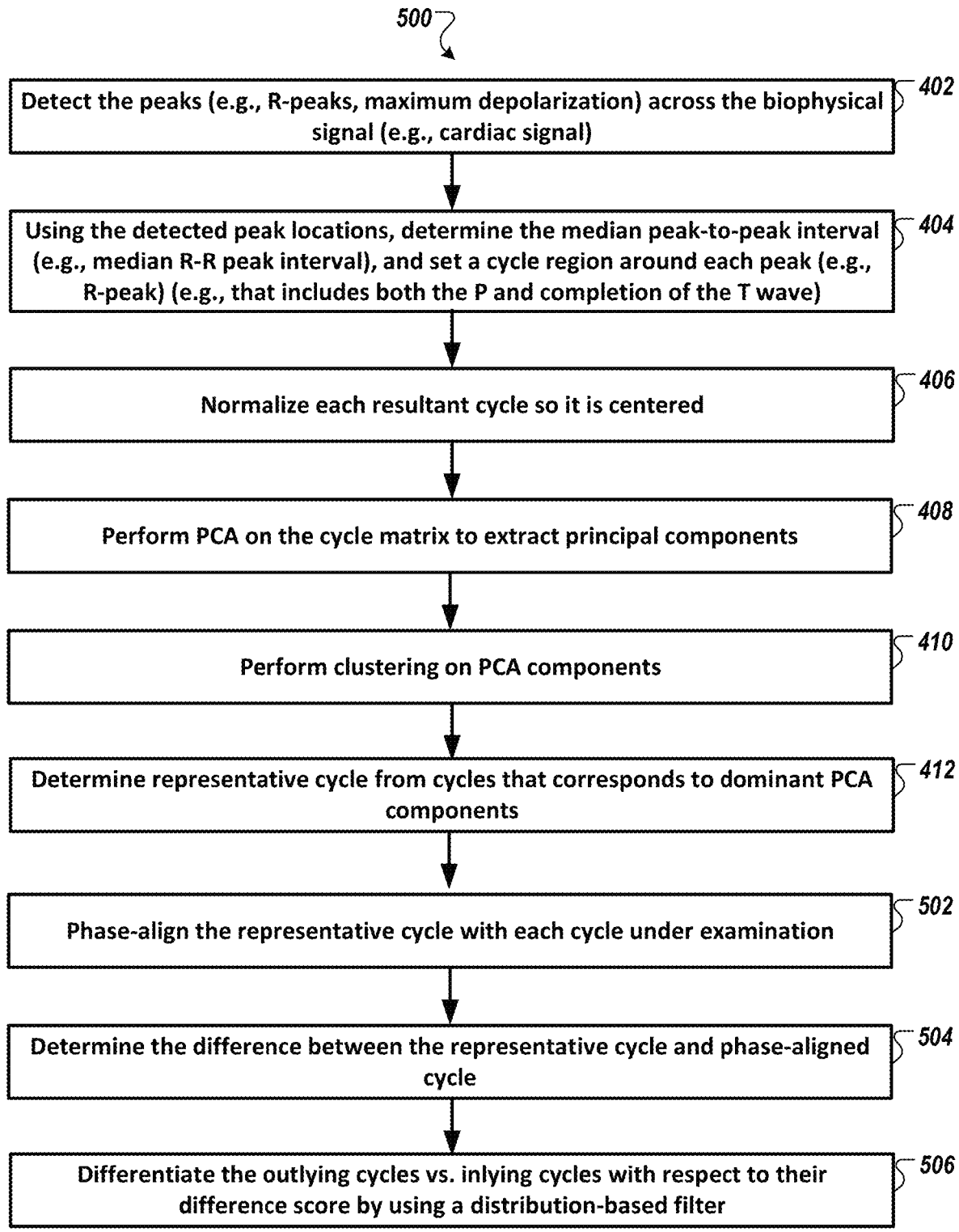
FIG. 5 is a diagram of an example method to quantify asynchronous noise contamination in a biophysical signal, in accordance with an illustrative embodiment.

Quantification of Skeletal-muscle Artifact Noise Contamination in a Biophysical Signal FIG. 5 is a diagram of an example method 500 to quantify, by a processor, skeletal-muscle-related artifact noise contamination in an acquired biophysical signal in accordance with an illustrative embodiment.

Method 500 includes steps 402-412 as discussed in relation to FIG. 4 and further includes the step of quantifying, by a processor, the distribution of differences between the determined representative cycle data set and the raw signal data set(s).

Method 500 further includes comparing each detected cycle in the raw signal data set cycle to the representative cycle data set. The comparison is performed by, first, phase-aligning (step 502) the representative cycle with each of the cycles under examination. In some embodiments, a method such as finding the maximum of the cross-correlation is used.

The comparison further includes determining (step 504) a difference between the representative cycle data set and the phase-aligned cycle under examination. In some embodiments, a method such as a correlation between the two signals is used. In other embodiments, a median absolute error is used. In yet other embodiments, a mean absolute error is used. If there is more than one representative cycle data set (as, e.g., detected through clustering on the two-dimensional PCA output), then the corresponding representative cycle data set that most matches a given cycle is used.

Figure 12:
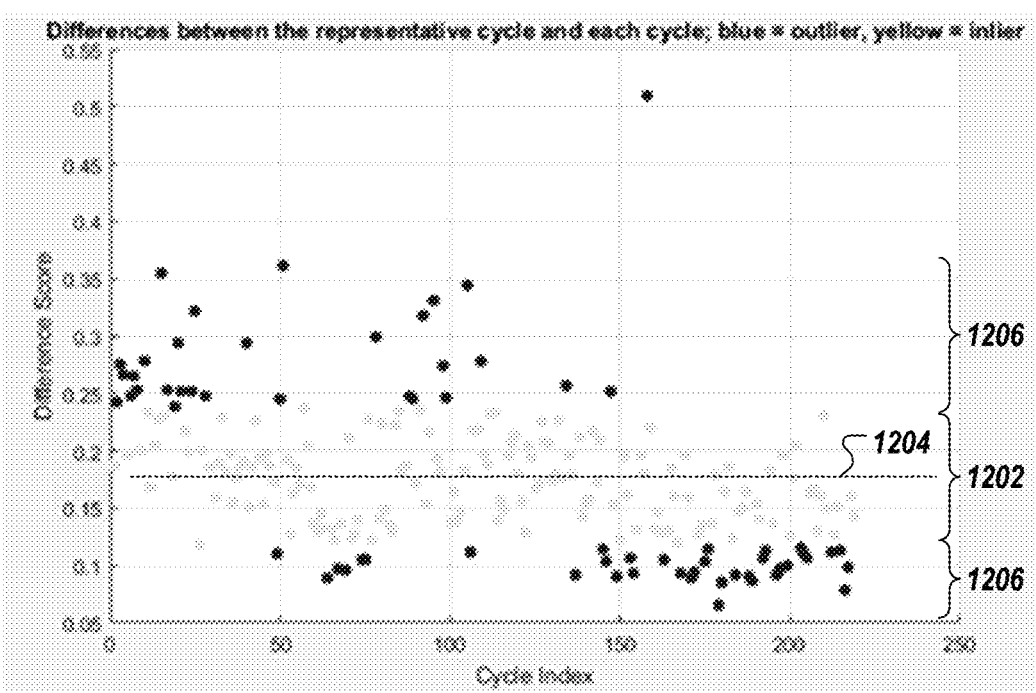
FIG. 12 is a plot of a distribution of difference score determined based on a comparison of the representative cycle data set and each evaluated cycle, in accordance with an illustrative embodiment.

The comparison further includes differentiating (step 506) outlying cycles and inlying cycles based on a difference score determined, e.g., using a distribution-based filter. In some embodiments, the distribution-based filter is configured to identify cycles having a standard deviation greater than one from the mean. FIG. 12 is a plot of a distribution of difference scores determined based on a comparison of the representative cycle data set and each of the evaluated cycles as a function of cycle index. As shown in FIG. 12, the inlying cycles are identified (e.g., in the region denoted by 1202) to be within one standard deviation of the mean of the distribution (shown as line 1204), and the outlying cycles are identified (e.g., in the regions denoted by 1206) to be outside the one standard deviation region from the mean. A final assessment of the contamination of the biophysical signal by the skeletal-muscle-related noise can be performed by taking a representative value of the inlying difference scores, such as the mean or the median.

Without wishing to be bound to a particular theory, the presence of outlying cycles can be attributed to several factors, including noise introduced by physiological variability of the biophysical signals and the underlying physiological system under study. For cardiac signals, the outlying cycles may be due to variability in the length and/or energy of depolarization or repolarization cycles, among others.

DISCUSSION

As noted above, quantification of asynchronous noise contamination such as skeletal-muscle-related artifact and noise contamination in a biophysical signal (such as a cardiac signal) can be complex. Skeletal-muscle-related artifact and noise, for example, can appear as in-band noise with respect to the biophysical signal—that is, it can occur in the same frequency range as the dominant components of the biophysical signal, typically around 0.5 Hz-80 Hz for cardiac signals and around 0.1-50 Hz for brain signals. Further, EMG can also have a similar amplitude as typical cardiac or brain waveform.

The similarity of skeletal-muscle-related artifact, and noise contamination to the biophysical signal, can cause issues for automated diagnostic analysis of such signals, and therefore, quantifying the level of skeletal-muscle-related artifact and noise contamination in a signal can facilitate the automated rejection of signals that are likely to be unsuccessful in subsequent analyses and/or the compensation for such contamination in subsequent analyses.

When quantifying the level of skeletal-muscle-related artifact and noise in a biophysical signal, particularly for cardiac signals, it is observed that skeletal-muscle-related artifact and noise is not in synchrony with the biophysical signal. Because the sources of the two are different (i.e., whereby the cardiac signal is derived from the summation of the action potentials of the cardiac myocytes, while the EMG is derived from the summation of the action potentials of the originating muscle (such as the pectoral muscles, biceps, triceps, etc.)), the sources are unlikely to share a deeper common source that could create synchronicity. Indeed, skeletal-muscle-related artifact and noise can be quantified by comparing each cardiac cycle to the idealized cardiac cycle for that patient, in which the gross differences can be accounted by the presence of skeletal-muscle-related artifact and noise contamination in the biophysical signal.

In the same way that skeletal-muscle-related artifact and noise quantification is a problem (e.g., skeletal-muscle-related artifact and noise being in-band with the physical signal), so is the challenge of skeletal-muscle-related artifact and noise denoising.

By leveraging the same insight from skeletal-muscle-related artifact and noise quantification, a time-series data set of the representative cycles can be generated to which a frequency-based analysis or time-based analysis can be performed to remove, or reduce, the skeletal-muscle-related artifact and noise and other asynchronous contamination.

Indeed, in some embodiments, a sample-by-sample comparison of the original signal in the frequency domain can be performed followed by a frequency domain denoising operation between the signals to derive the denoised signals based on a spectral mask determined from the representative cycle vector and using that to mask noise features in the original signal in the frequency domain. The exemplified denoising approach leverages the robust information contained in the representative cycle along with the information on the variation of the biophysical signal contained in the raw data.

Figure 13A:
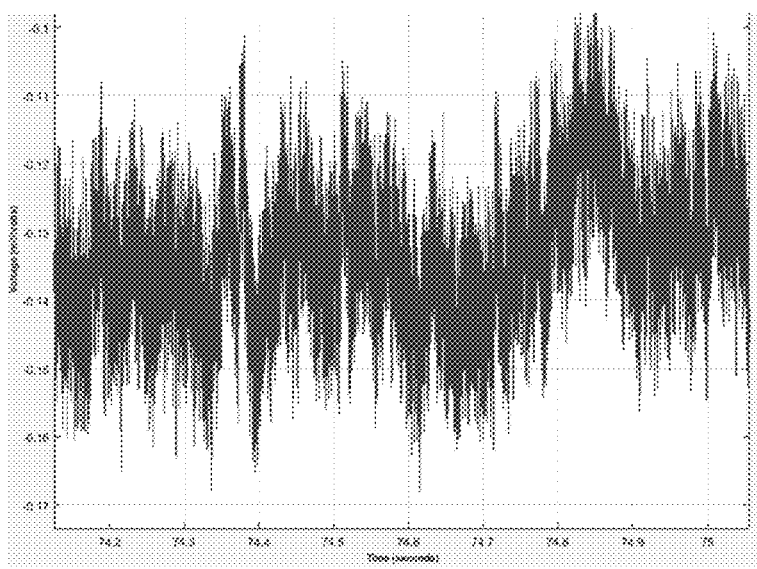
FIGS. 13A, 13B, and 13C show an example wide-band cerebral phase gradient signal data set acquired from the measurement system of FIG. 1A, in accordance with an illustrative embodiment.
Figure 13B:
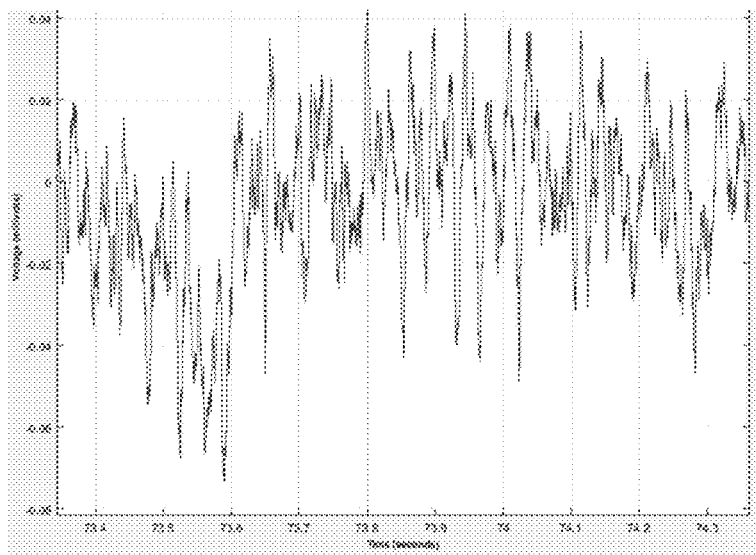
Figure 13C:
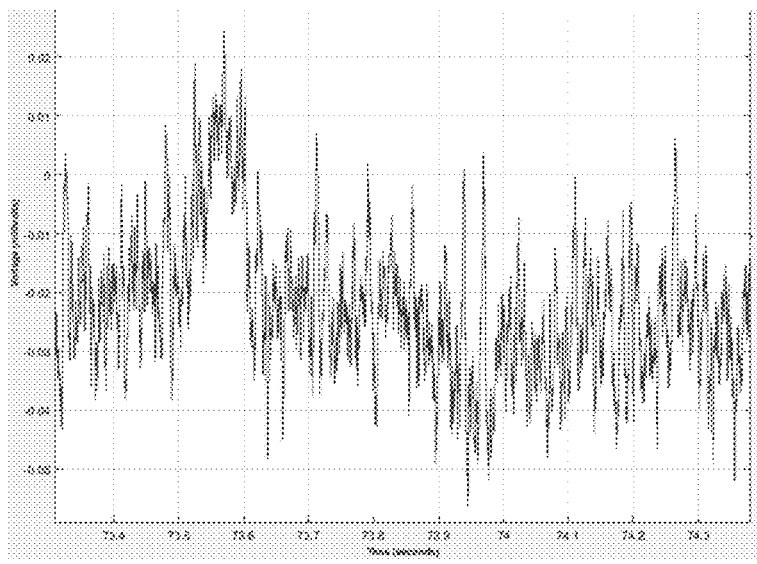
Figure 14:
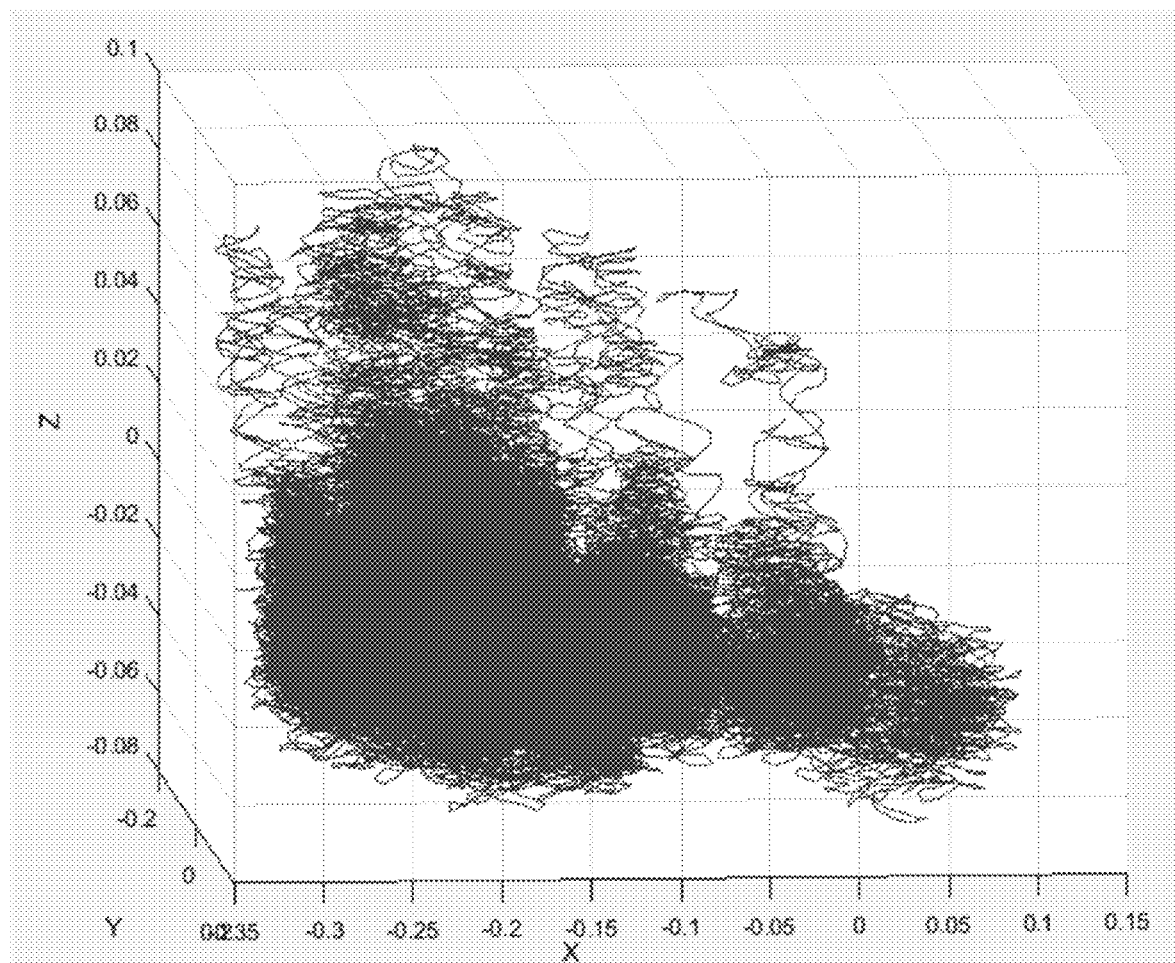
FIG. 14 illustrates the wide-band cerebral phase gradient signals of FIGS. 13A-13C presented in phase space, in accordance with an illustrative embodiment.

The exemplified methods and systems are demonstrated above in relation to cardiac signals. It is noted that exemplified methods and systems can be applied to brain signals and other biophysical signals. FIGS. 13A, 13B, and 13C show an example wide-band cerebral phase gradient signal data set acquired from the measurement system 102 of FIG. 1A. FIG. 14 illustrates the wide-band cerebral phase gradient signals of FIGS. 13A-13C presented in phase space. Indeed, the wide-band cerebral phase gradient signal is a quasi-periodic system and is similar to a cardiac wide-band cardiac phase gradient signal in that regard, to which the exemplified methods and systems can be applied.

Device Normalization Process

In another aspect, the asynchronous contamination removal operation as described herein can be used to normalize cardiac signals acquired from multiple and different acquisition platforms, e.g., prior to subjecting data acquired from such platform for machine-learning-based disease association. The normalization is driven, at least in part, by knowledge of theoretical topological differences and insights from deep learning. The device normalization process can be applied to data acquired from multiple acquisition devices, e.g., that are from two or more different generations, to increase similarity (as guided by both machine learning and electrical engineering theory) between the groups of signals that can improve the machine learning training process.

Figure 15:
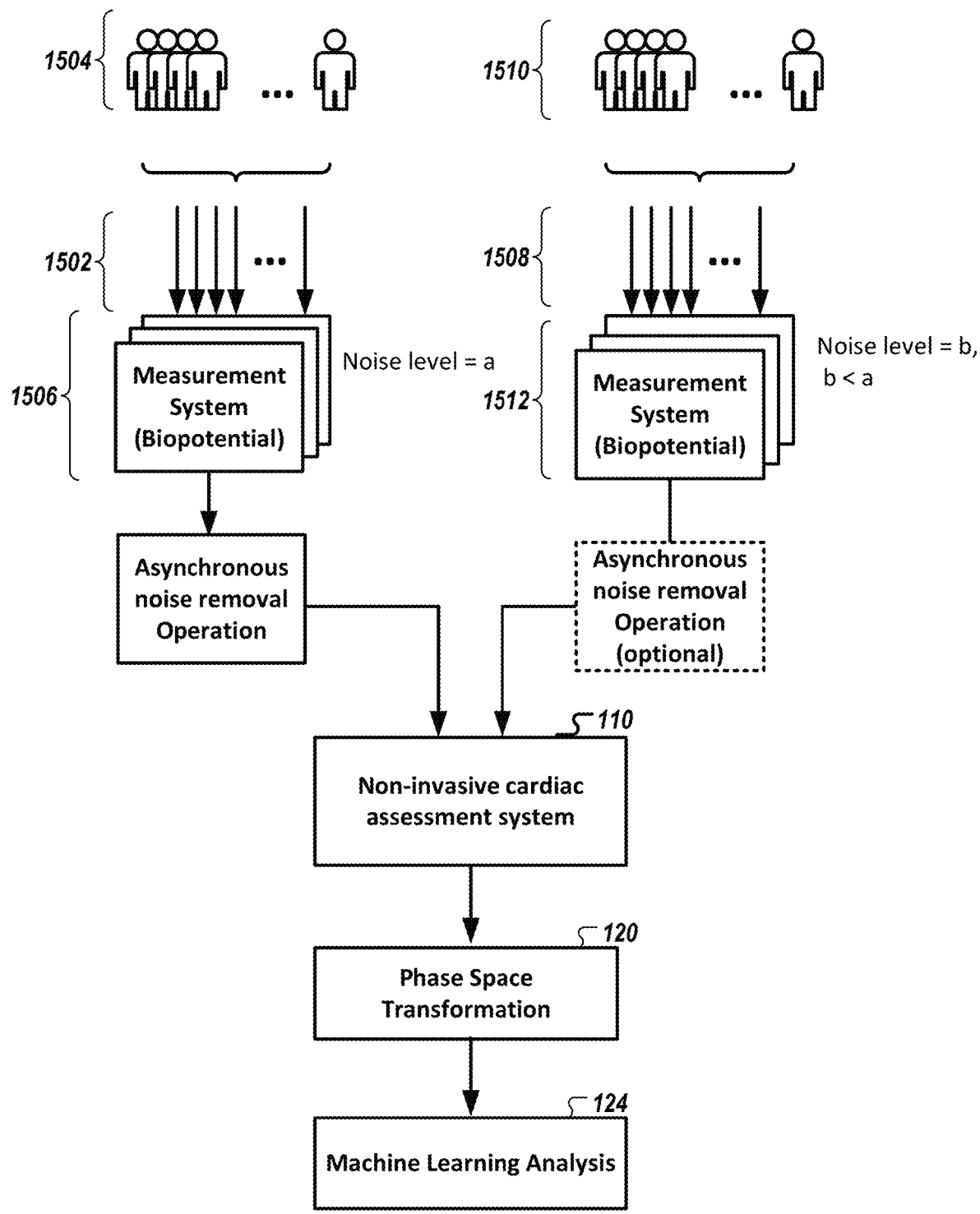
FIG. 15 is a diagram of a method to normalize a first set of data sets acquired with a first set of biophysical-signal measurement equipment and a second set of data sets acquired with a second set of biophysical-signal measured equipment such that the first set of data sets may be analyzed with the second set of data sets in a machine learning operation, in accordance with an illustrative embodiment.

FIG. 15 is a diagram of a method to normalize a first set of data sets acquired with a first set of biophysical-signal measurement equipment and a second set of data sets acquired with a second set of biophysical-signal measurement equipment such that the first set of data sets may be analyzed with the second set of data sets in a machine learning operation. As shown in FIG. 15, a first set of cardiac signal data sets (e.g., shown as 1502) of a first set of subjects (e.g., shown as 1504) is acquired with a first set of biophysical-signal measurement equipment (e.g., shown as 1506), and a second set of cardiac signal data sets (e.g., shown as 1508) of a second set of subjects (e.g., shown as 1510) is acquired with a second set of biophysical-signal measurement equipment (e.g., shown as 1512).

In some embodiments, the first set of cardiac signal data sets (e.g., 1502) is processed with a processor to remove asynchronous noise contamination as described in relation to FIG. 1 so as to improve the similarity between the first set of cardiac signal data sets and the second set of cardiac signal data sets and to facilitate the use of the first set of cardiac signal data sets and the second set of cardiac signal data sets in a same training data set for a machine learning operation.

In some embodiments, the second set of cardiac signal data sets (e.g., 1508) is processed with a processor to remove asynchronous noise contamination as described in relation to FIG. 1A so as to improve the similarity between the first set of cardiac signal data sets and the second set of cardiac signal data sets.

Experimental Results

A Coronary Artery Disease-Learning Algorithm Development (CADLAD) study was undertaken involving two distinct stages to support the development and testing of machine-learned algorithms. In stage 1, paired clinical data were used to guide the design and development of the pre-processing, feature extraction, and machine learning steps. That is, the collected clinical study data is split into three cohorts: Training (50%), validation (25%), and verification (25%). Similar to the steps described above for processing signals from a patient for analysis, each signal is first pre-processed to clean and normalize the data. Following these processes, a set of features are extracted from the signals in which each set of features is paired with a representation of the true condition—for example, the binary classification of the presence or absence of significant CAD. The final output of this stage is a fixed algorithm embodied within a measurement system. In Stage 2 of the CADLAD study, the machine-learned algorithms will be used to provide a determination of significant CAD against a pool of previously untested clinical data. The criteria for a disease are established as that defined in the American College of Cardiology (ACC) clinical guidelines, specifically as greater than 70% stenosis by angiography or less than 0.80 fraction-flow by flow wire.

For part of the study, a first set of cardiac signal data sets associated with an earlier acquisition hardware (e.g., "Gen 1") (e.g., the measurement system 104) is processed to remove the asynchronous noise contamination as described in relation to FIG. 1A to facilitate of use of the first set of cardiac signal data sets and a second set of the cardiac signal data sets (acquired with later acquisition hardware, e.g., "Gen 2") (e.g., the measurement system 104) as training data set for the machine learning operation in the CADLAD study. Further description of an example earlier acquisition hardware (e.g., comprising a unipolar sensing front end) can be found in U.S. Publication No. 2017/0119272, which is incorporated by reference herein in its entirety, and further description of later acquisition hardware (e.g., comprising a bipolar sensing front end) can be found in U.S. application Ser. No. 15/911,047, which is also incorporated by reference herein in its entirety.

The assessment system 110, in some embodiments, automatically and iteratively explores combinations of features in various functional permutations with the aim of finding those combinations which can successfully match a prediction based on the features. To avoid overfitting of the solutions to the training data, the validation set is used as a comparator. Once candidate predictors have been developed, they are then manually applied to a verification data set to assess the predictor performance against data that has not been used at all to generate the predictor. Provided that the data sets are sufficiently large, the performance of a selected predictor against the verification set will be close to the performance of that predictor against new data.

Figure 16:
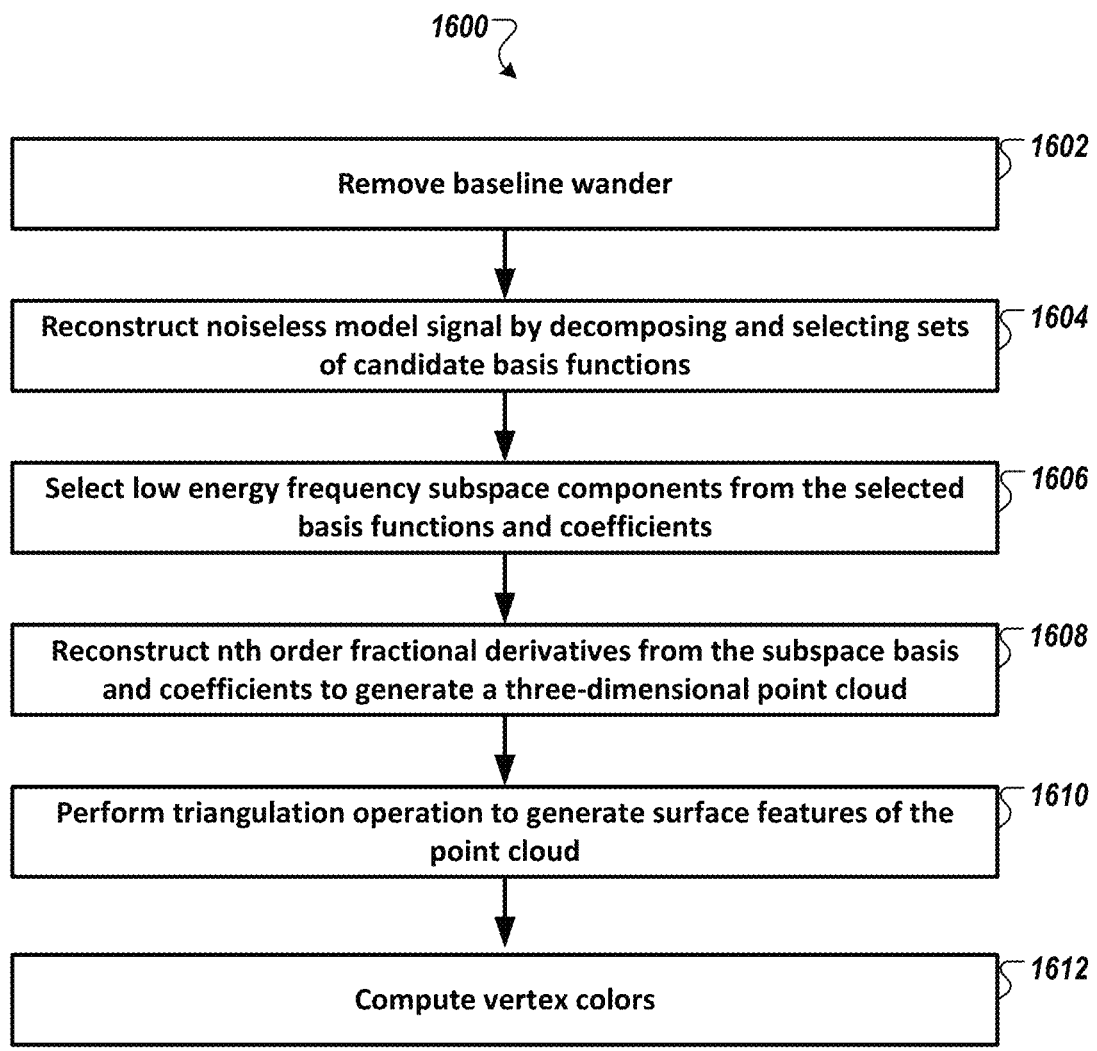
FIG. 16 is an example method of analysis by the non-invasive cardiac assessment system in accordance with an implementation of the present disclosure.

FIG. 16 is an example method 1600 of generating and analyzing a phase space volumetric object 122 by the non-invasive cardiac assessment system 110 in accordance with an implementation of the present disclosure. Other implementations may become evident to one of ordinary skill in the art based on this disclosure. The method 1600 includes, in some embodiments, removing (operation 1602)

a baseline wander from the raw differential channel signal of phase-gradient biophysical-signal data set 108. In some implementations, the raw differential channel signal is derived from six signals simultaneously sampled by the measurement system 102.

In some implementations, six simultaneously sampled signals are captured from a resting subject as the raw differential channel signal data set in which the signals embed the inter-lead timing and phase information of the acquired signals, specific to the subject. Geometrical contrast arising from the interference in the phase plane of the depolarization wave with the other orthogonal leads can be used, which can facilitate the superimposition of phase space information on a three-dimensional representation of the heart. Noiseless subspaces further facilitate the observation of the phase of these waves. That is, the phase of the orthogonal leads carries the information about the structure and generates geometrical contrast in the image. Phase-contrast takes advantage of the fact that different bioelectric structures have different impedances, and so spectral and non-spectral conduction delays and bends the trajectory of phase space orbit through the heart by different amounts. These small changes in trajectory can be normalized and quantified beat to beat and corrected for abnormal or poor lead placement, and the normalized phase space integrals can be mapped to a geometric mesh for visualization.

In some implementations, the raw differential channel signal data set is normalized, and baseline wander is removed using a modified moving average filter. For example, in some implementations, the baseline wander is extracted from each of the raw differential channel signals using a median filter with an order of 1500 milliseconds, smoothed with a 1-Hz low-pass filter, and subtracted from the signals. The bias is then removed from the resulting signals by subtracting estimations of the signals using maximums of probability densities calculated with a kernel smoothing function. All of the signals, or a portion thereof, may be divided by their respective interquartile ranges to complete the normalization process.

The method 1600 then includes, in some embodiments, reconstructing (operation 1604) a noiseless model signal by decomposing and selecting sets of candidate basis functions to create a sparse mathematical model. In some implementations, a Modified Matching Pursuit (MMP) algorithm is used to find a noiseless model of the raw differential channel signals. Other sparse approximation algorithms can be used, including, and not limited to, evolvable mathematical models, symbolic regression, orthogonal matching pursuit, LASSO, linear models optimized using cyclical coordinate descent, orthogonal search, fast orthogonal search, and cyclical coordinate descent. In some implementations, the reconstructing operation 504 generates a model as a function with a weighted sum of basis functions in which basis function terms are sequentially appended to an initially empty basis to approximate a target function while reducing the approximation error.

The method 1600 then includes, in some embodiments, selecting (operation 506) subspace components (e.g., low energy frequency subspace components) from the selected basis functions and coefficients. The low-energy subspace components comprise a model reconstructed by using only the X % low magnitude subset coefficients (frequency content), contributing least to the modeling error. Low-energy subspace components, in some implementations, includes higher-order candidate terms that are later selected, in the phase space coordinates, as part of the sparse representation of a signal. That is, the last 5 percent, 10 percent, 15 percent, 20 percent, 25 percent, 30 percent of the candidate terms (as the higher-order candidate terms) last selected via the sparse approximation is used. Other percentage values can be used.

The method 1600 then includes, in some embodiments, reconstructing (operation 1608) a pre-defined set of $n^{th}$ order fractional-calculus result sets (e.g., via a numeric fractional-calculus operation) to generate a three-dimensional point cloud defining, in part, the phase space volumetric object 122. In some implementations, the fractional-calculus operation is based on Grünwald-Letnikov fractional-derivative method. In some implementations, the fractional derivative operation is based on the Lubich's fractional linear multi-step method. In some implementations, the fractional-calculus operation is based on the fractional Adams-Moulton method. In some implementations, the fractional-calculus operation is based on the Riemann-Liouville fractional derivative method. In some implementations, the fractional derivative operation is based on Riesz fractional derivative method. Other methods of performing fractional calculus may be used.

The method 1600 then includes, in some implementations, performing (1610) triangulation operation to generate surface features (i.e., face) of the point cloud. In some implementations, Alpha Hull triangulation with a pre-pre-determined radius (a) is performed on the reconstructed noiseless model signals. In other implementations, Delaunay triangulation, alpha shapes, ball pivoting, Mesh generation, Convex Hull triangulation, and the like, is used.

The method 1600 then includes, in some implementations, computing (1612) one or more values for each of the vertices in the point cloud. The vertex values, in some implementations, are scaled over a presentable color range. The vertex values, in some implementations, is a variance between a modeled channel data set (e.g., X-axis data set, Y-axis data set, or Z-axis data set) a base-line raw channel data set (e.g., corresponding X-axis data set, Y-axis data set, or Z-axis data set). In some implementations, the variance is determined by subtracting data points of the baseline raw channel data set with the corresponding data points of the modeled channel data set. The modeled channel data set, in some implementations, is based on a sparse approximation of the baseline raw channel data set to generate a reconstructed noiseless signal of the baseline raw channel data. In some implementations, each face of the phase space volumetric object 122 is assigned a face color value triangularly interpolated among neighboring bounding vertex color values (e.g., 3 bounding vertex colors).

In some implementations, various views of the phase space volumetric object 122 are captured for presentation as computed phase space tomographic images, e.g., via a web portal, to a physician to assist the physician in the assessment of presence or non-presence of pulmonary arterial hypertension. In some implementations, the phase space volumetric object or the computed phase space tomographic images are assessed by a trained neural network classifier configured to assess for the presence or non-presence of pulmonary arterial hypertension. In some implementations, the computed tomographic images are presented (e.g., a set of two-dimensional views) alongside the results of a machine-generated prediction to assist the physician in making a diagnosis.

In other implementations, the phase space volumetric object 122 is analyzed in subsequent machine learning operations (e.g., image-based machine learning operations or feature-based machine learning operations) to determine one or more coronary physiological parameters. In some implementations, the assessment system 110 is configured to determine a volume metric (e.g., alpha hull volume) of the phase space volumetric object 122. In some implementations, the assessment system 110 is configured to determine a number of distinct bodies (e.g., distinct volumes) of the generated phase space volumetric object 122. In some implementations, the assessment system 110 is configured to assess a maximal color variation (e.g., color gradient) of the generated phase space volumetric object 122. In some implementations, all these features are assessed from phase space volumetric object 122 as a mathematical feature.

In some implementations, the mathematical features of the phase space volumetric object 122 are extracted along with hundreds of other distinct mathematical features that represent specific aspects of the biophysical signals collected. A feature extraction engine of the assessment system 110 may extract each feature as a specific formula/algorithm. In some implementations, when the feature extraction process is applied to an incoming biophysical signal, the output is a matrix of all calculated features, which includes a list, for example, of over hundreds of real numbers; one number per feature in which each feature represents one or more aspects of the signal's dynamical, geometrical, fractional calculus, chaotic, and/or topological properties.

A machine learning algorithm (e.g., meta-genetic algorithm), in some implementations, is used to generate predictors linking aspects of the phase space model (e.g., pool of features) across a population of patients representing both positive (i.e., have disease) and negative (i.e., do not have disease) cases to detect the presence of myocardial tissue associated with pulmonary arterial hypertension. In some implementations, the performances of the candidate predictors are evaluated through a verification process against a previously unseen pool of patients. In some implementations, the machine learning algorithm invokes a meta-genetic algorithm to automatically select a subset of features drawn from a large pool. This feature subset is then used by an Adaptive Boosting (AdaBoost) algorithm to generate predictors to diagnose pulmonary arterial hypertension across a population of patients representing both positive and negative cases. The performances of the candidate predictors are determined through verification against a previously unseen pool of patients. A further description of the AdaBoost algorithm is provided in Freund, Yoav, and Robert E. Schapire, "A decision-theoretic generalization of on-line learning and an application to boosting," European conference on computational learning theory. Springer, Berlin, Heidelberg (1995), which is incorporated by reference herein in its entirety.

In some implementations, the assessment system 110 generates one or more images of a representation of the phase space volumetric object 122 in which the vertices, face triangulations, and vertex colors are presented. In some implementations, multiple views of the representation are generated and included in a report. In some implementations, one or more images are presented as a three-dimensional object that can be rotated, scaled, and/or panned based on the user's inputs. Indeed, such presentation can be used to be assessed visually by a skilled operator to determine whether a subject has the presence or non-presence of pulmonary arterial hypertension.

Neural Network Classification

The three-dimensional phase-space volumetric object or the computed phase-space tomographic images can be directly evaluated by a trained neural network classifier to determine the presence or non-presence of pulmonary arterial hypertension. In some implementations, the neural network classifier may be a neural network trained on a set of grayscale tomographic images which are paired with coronary angiography results assessed for presence and non-presence of pulmonary arterial hypertension. In some implementations, a neural network-based nonlinear classifier is used. In some implementations, the neural network-based non-linear classifier is configured to map individual pixels from the generated tomographic images to a binary disease-state prediction (i.e., the condition exists or does not exist) or an estimated physiological characteristic. In some implementations, the neural network's weights, which govern this mapping, are optimized using gradient descent techniques.

Examples of a disease state prediction can include, but are not limited to, presence/non-presence of significant coronary arterial disease, presence/non-presence of pulmonary hypertension, presence/non-presence of pulmonary arterial hypertension, presence/non-presence of pulmonary hypertension due to left heart disease, presence/non-presence of pulmonary hypertension due to lung disease, presence/non-presence of pulmonary hypertension due to chronic blood clots, etc.

Examples of an estimated physiological characteristic can include, but are not limited to, fractional flow reserve, degree of stenosis, degree of ischemia, blood glucose levels, cardiac chamber size, and mechanical function, etc.

Further examples of processing that may be used with the exemplified method and system are described in: U.S. Pat. No. 9,289,150, entitled "Non-invasive Method and System for Characterizing Cardiovascular Systems"; U.S. Pat. No. 9,655,536, entitled "Non-invasive Method and System for Characterizing Cardiovascular Systems"; U.S. Pat. No. 9,968,275, entitled "Non-invasive Method and System for Characterizing Cardiovascular Systems"; U.S. Pat. No. 8,923,958, entitled "System and Method for Evaluating an Electrophysiological Signal"; U.S. Pat. No. 9,408,543, entitled "Non-invasive Method and System for Characterizing Cardiovascular Systems and All-Cause Mortality and Sudden Cardiac Death Risk"; U.S. Pat. No. 9,955,883, entitled "Non-invasive Method and System for Characterizing Cardiovascular Systems and All-Cause Mortality and Sudden Cardiac Death Risk"; U.S. Pat. No. 9,737,229, entitled "Noninvasive Electrocardiographic Method for Estimating Mammalian Cardiac Chamber Size and Mechanical Function"; U.S. Pat. No. 10,039,468, entitled "Noninvasive Electrocardiographic Method for Estimating Mammalian Cardiac Chamber Size and Mechanical Function"; U.S. Pat. No. 9,597,021, entitled "Noninvasive Method for Estimating Glucose, Glycosylated Hemoglobin and Other Blood Constituents"; U.S. Pat. No. 9,968,265, entitled "Method and System for Characterizing Cardiovascular Systems From Single Channel Data"; U.S. Pat. No. 9,910,964, entitled "Methods and Systems Using Mathematical Analysis and Machine Learning to Diagnose Disease"; U.S. Patent Publication No. 2017/0119272, entitled "Method and Apparatus for Wide-Band Phase Gradient Signal Acquisition"; PCT Publication No. WO2017/033164, entitled "Method and Apparatus for Wide-Band Phase Gradient Signal Acquisition"; U.S. Patent Publication No. 2018/0000371, entitled "Non-invasive Method and System for Measuring Myocardial Ischemia, Stenosis Identification, Localization and Fractional Flow Reserve Estimation"; PCT Publication No. WO2017/221221, entitled "Non-invasive Method and System for Measuring Myocardial Ischemia, Stenosis Identification, Localization and Fractional Flow Reserve Estimation"; U.S. Pat. No. 10,292,596, entitled "Method and System for Visualization of Heart Tissue at Risk"; U.S. patent application Ser. No. 16/402,616, entitled "Method and System for Visualization of Heart Tissue at Risk"; U.S. Patent Publication No. 2018/0249960, entitled "Method and System for Wide-band Phase Gradient Signal Acquisition"; U.S. patent application Ser. No. 16/232,801, entitled "Method and System to Assess Disease Using Phase Space Volumetric Objects"; PCT Application No. IB/2018/060708, entitled "Method and System to Assess Disease Using Phase Space Volumetric Objects"; U.S. Patent Publication No. US2019/0117164, entitled "Methods and Systems of De-Noising Magnetic-Field Based Sensor Data of Electrophysiological Signals"; U.S. patent application Ser. No. 16/232,586, entitled "Method and System to Assess Disease Using Phase Space Tomography and Machine Learning"; PCT Application No. PCT/IB2018/060709, entitled "Method and System to Assess Disease Using Phase Space Tomography and Machine Learning"; U.S. patent application Ser. No. 16/725,402, entitled "Method and System to Assess Disease Using Phase Space Tomography and Machine Learning"; U.S. patent application Ser. No. 16/429,593, entitled "Method and System to Assess Pulmonary Hypertension Using Phase Space Tomography and Machine Learning"; U.S. patent application Ser. No. 16/725,416, entitled "Method and System for Automated Quantification of Signal Quality"; U.S. patent application Ser. No. 16/725,430, entitled "Method and System to Configure and Use Neural Network To Assess Medical Disease"; U.S. Patent Provisional Application No. 62/785,158; U.S. patent application Ser. No. 15/653,433, entitled "Discovering Novel Features to Use in Machine Learning Techniques, such as Machine Learning Techniques for Diagnosing Medical Conditions"; U.S. patent application Ser. No. 15/653,431, entitled "Discovering Genomes to Use in Machine Learning Techniques"; U.S. Provisional application Ser. No. 16/831,380, entitled "Method and System to Assess Disease Using Dynamical Analysis of Cardiac and Photoplethysmographic Signals", each of which is incorporated by reference herein in its entirety.

Unless otherwise expressly stated, it is in no way intended that any method set forth herein be construed as requiring that its steps be performed in a specific order. Accordingly, where a method claim does not actually recite an order to be followed by its steps, or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow; plain meaning derived from grammatical organization or punctuation; the number or type of embodiments described in the specification.

While the methods and systems have been described in connection with certain embodiments and specific examples, it is not intended that the scope be limited to the particular embodiments set forth, as the embodiments herein are intended in all respects to be illustrative rather than restrictive.

The methods, systems, and processes described herein may be used to generate stenosis and FFR outputs for use in connection with procedures such as the placement of vascular stents within a vessel such as an artery of a mammalian (e.g., human) subject and other interventional and surgical system or processes. In one embodiment, the methods, systems, and processes described herein can be configured to use the FFR/stenosis outputs to determine and/or modify intra operation, a number of stents to be placed in a mammalian (e.g., human), including their optimal location of deployment within a given vessel, among others.

Examples of other biophysical signals that may be analyzed in whole, or in part, using the exemplary methods and systems include, but are not limited to, an electrocardiogram (ECG) data set, an electroencephalogram (EEG) data set, a gamma synchrony signal data set; a respiratory function signal data set; a pulse oximetry signal data set; a perfusion data signal data set; a quasi-periodic biological signal data set; a fetal ECG data set; a blood pressure signal; a cardiac magnetic field data set, and a heart rate signal data set.

The exemplary analysis can be used to identify various pathologies and conditions including, but are not limited to heart disease, cardiac arrhythmia, diabetic autonomic neuropathy, Parkinson's disease, forms of epilepsy, brain injury, altered state of cognition, stability of a heart at different heart rates, the effectiveness of medication, ischemic, silent ischemia, atrial fibrillation, ventricular fibrillation, ventricular tachycardia, blood vessel block, pulmonary hypertension, attention deficit disorder, etc.

What is claimed is:

1. A method to filter asynchronous noise from an acquired biophysical-signal data set, the method comprising:
   receiving, by a processor, a biophysical-signal data set of a subject;
   determining, by the processor, at least one template-signal vector data set characteristic of a representative quasi-periodic signal pattern of the subject from a plurality of detected quasi-periodic cycles detected in the received biophysical-signal data set;
   applying, by the processor, the at least one determined template-signal vector data set to one or more denoising vector data sets, wherein the one or more denoising vector data sets collectively have a vector length corresponding to a vector length of a portion of the received biophysical-signal data set to be filtered, and wherein the at least one determined template-signal vector data set is i) applied for each of the detected cycles determined to be present in the portion of received cardiac signal data set to be filtered and ii) varied in length to match the vector length of a corresponding detected cycle of the portion of the received biophysical-signal data set to be filtered; and
   generating a filtered biophysical-signal data set of the biophysical-signal data set, or a portion thereof, by merging the portion of the received biophysical-signal data set to be filtered and the one or more generated denoising vector data sets.

2. The method of claim 1 further comprising:
   receiving, by the processor, one or more additional biophysical signal data sets each contemporaneously acquired from the subject with the biophysical signal data set;
   determining, by the processor, at least one template-signal vector data set characteristic of a representative quasi-periodic signal pattern of the subject from a plurality of detected heart-beat cycles detected in each of the received one or more additional biophysical signal data sets;
   applying, by the processor, for each of the received one or more additional biophysical signal data sets, a plurality of determined template-signal vector data sets to one or more denoising vector data sets in a repeating manner, wherein the one or more denoising vector data sets collectively have a vector length corresponding to a vector length of a portion of the received additional biophysical signal data sets to be filtered, and wherein each of the plurality of determined template-signal vector data sets is i) applied for each of the detected cycles determined to be present in the portion of received additional biophysical signal data sets to be filtered and ii) varied in length to match the vector length of a corresponding detected cycle of the portion of the received additional biophysical signal data sets to be filtered; and generating a filtered biophysical signal data set of the biophysical signal data set, or a portion thereof, by merging the portion of the received biophysical signal data set to be filtered and the one or more generated denoising vector data sets.

3. The method of claim 1, wherein the step of determining the at least one template-signal vector data set characteristic of the representative quasi-periodic signal pattern comprises:

determining, by the processor, a plurality of signal features characteristically distinct in the received biophysical signal data set or a portion thereof;

determining, by the processor, a plurality of cycle regions between each of the plurality of determined signal features;

aligning, by the processor, each of the plurality of cycle regions to each other to a same aspect of the plurality of signal features or another set of signal features located in each of the cycle regions; and determining, by the processor, each point of the at least one template-signal vector data set using a mean operation or a median operation performed for each set of points among the plurality of cycle regions.

4. The method of claim 1, wherein the received biophysical-signal data set comprises a cardiac signal data set, and wherein the plurality of signal features are selected from the group consisting of: R-peaks in the received cardiac signal data set or a portion thereof, S-peaks in the received cardiac signal data set or a portion thereof, T-peaks in the received cardiac signal data set or a portion thereof, Q-peaks in the received cardiac signal data set or a portion thereof, and P-peaks in the received cardiac signal data set or a portion thereof.

5. The method of claim 1, wherein the received biophysical-signal data set comprises a cardiac signal data set, and wherein the plurality of signal features correspond to R-peaks in the received cardiac signal data set or a portion thereof.

6. The method of claim 1, wherein the step of determining the at least one template-signal vector data set characteristic of the representative quasi-periodic pattern further comprises:

determining, by the processor, a normalizing parameter derived from each the plurality of cycle regions.

7. The method of claim 1, wherein the step of determining the at least one template-signal vector data set characteristic of the representative quasi-periodic signal pattern further comprises:

normalizing, by the processor, values, or a parameter derived therefrom, of each of the plurality of cycle regions to a pre-defined scale.

8. The method of claim 1, wherein the step of determining the at least one template-signal vector data set characteristic of the representative quasi-periodic signal pattern further comprises:

performing, by the processor, clustering-based analysis of the plurality of cycle regions to determine presence of more than one dominant cycle morphologies, wherein a template-signal vector is determined for each determined dominant cycle morphology.

9. The method of claim 1, wherein the plurality of cycle regions comprises cycles that are neighboring one another.

10. The method of claim 9, wherein the cycles that are neighboring one another overlaps in part to one another.

11. The method of claim 9, wherein the cycles that are neighboring one another do not overlap to one another.

12. The method of claim 9, wherein the filtered biophysical signal data set is generated by using two or more template-signal vector data sets from two or more group of cycles of the plurality of cycle regions, wherein the two or more groups of cycles of the plurality of cycle regions are neighboring one another.

13. The method of claim 1, wherein the filtered biophysical signal data set is generated in near real-time as the biophysical signal is acquired.

14. The method of claim 1, wherein the filtered biophysical-signal data set is generated following completed acquisition of the biophysical signal.

15. The method of claim 1, wherein the one or more denoising vector data sets are arranged as a 1-dimensional vector.

16. The method of claim 1, wherein the one or more denoising vector data sets are arranged as an N-dimensional vector, wherein N corresponds to a number of detected cycles determined to be present in the portion of received biophysical signal data set to be filtered.

17. The method of claim 1, wherein the step of applying the plurality of the determined template-signal vector data sets to one or more denoising vector data sets comprises:

initializing, by the processor, the one or more denoising vector data set as a 1-dimensional vector having a length corresponding to that of the portion of received biophysical signal to be filtered; and duplicating, by the processor, the determined template-signal vectors in the 1-dimensional vector so as to align at least a data point associated with a peak of the determined template-signal vectors to each peak determined in the received biophysical signal to be filtered.

18. The method of claim 17, wherein, during the duplication step, conflict portions of a currently duplicating template-signal vector data set are assigned average values with respect to corresponding portions of a previously duplicated template-signal vector data set to which the currently duplicating template-signal vector data set has a conflict.

19. The method of claim 17, wherein, during the duplication step, empty regions in the 1-dimensional vector between a currently duplicating template-signal vector data set and a previously duplicated template-signal vector data set are stored with values interpolated between a last filled value and a next filled value around the empty region.

20. The method of claim 1, wherein the window-based operation comprises:

scaling, by the processor, the portion of the received biophysical signal data set to be filtered with a plurality of window functions having a pre-defined window length to generate a modified biophysical signal data set;

scaling, by the processor, the one or more generated denoising vector data sets with the plurality of window functions to generate a modified denoising vector data sets;

determining, by the processor, an envelope of the modified denoising vector data sets;

converting, by the processor, via a FFT operation, the envelope of the modified denoising vector data sets and of the portion of the received biophysical signal data set to be filtered to the frequency domain;

performing, by the processor, a weighted average operation of the FFT envelope of the modified denoising vector data sets and of the modified biophysical signal data set using a static, or a set of dynamic, interpolation coefficients to generate a resulting data set; and converting, by the processor, via an inverse FFT operation, the resulting data set to a time series data set as the filtered biophysical signal data set of the biophysical signal.

21. A method of normalizing a first set of data sets acquired with a set of first measurement equipment and a second set of data sets acquired with a second set of measurement equipment such that the first set of data sets is analyzable with the second set of data sets in a machine learning operation, the method comprising:

receiving, by a processor, a set of biophysical-signal data sets of a subject acquired with a set of first measurement equipment;

determining, by the processor, at least one template-signal vector data set characteristic of a representative quasi-periodic signal pattern of the subject from a plurality of detected quasi-periodic signal cycles detected in the received biophysical-signal data set;

applying, by the processor, a plurality of the determined template-signal vector data sets, or a vector selected from the group thereof, to one or more denoising vector data sets, wherein the one or more denoising vector data sets collectively have a vector length corresponding to a vector length of a portion of the received biophysical signal data set to be filtered, wherein each applied template-signal vector data set is i) applied for each of the detected cycles determined to be present in the portion of received biophysical signal data set to be filtered and ii) varied in length to match the vector length of a corresponding detected cycle of the portion of the received biophysical signal data set to be filtered; and generating a filtered biophysical signal data set associated with the biophysical signal data set, or a portion thereof, as a normalized data set of the biophysical signal, wherein the filtered biophysical signal is generated by merging the portion of the received biophysical signal to be filtered and the one or more generated denoising vectors, wherein the normalized data set associated with the biophysical signal acquired with the first measurement equipment is analyzable as a machine-learning training data set along with a second data set acquired with a second measured equipment.

22. The method of claim 21, wherein a data set of the received biophysical signal comprises data captured from sensors selected from the group consisting of a 12-lead surface potential sensing electrode system, an intracardiac electrocardiogram, a Holter electrocardiogram, a 6-lead differential surface potential sensing electrode system, a 3-lead orthogonal surface potential sensing electrode system, and a single lead potential sensing electrode system.

23. The method of claim 22, wherein a data set of the received biophysical signal comprises wide-band cardiac phase gradient cardiac signal data derived from biopotential signals simultaneously captured from a plurality of surface electrode placed on surfaces of a body in proximity to a heart.

24. A method of rejecting an acquired biophysical signal, the method comprising:

receiving, by a processor, a biophysical-signal data set of a subject;

comparing, by the processor, the received biophysical-signal data set to at least one template-signal vector data set characteristic of a representative quasi-periodic pattern within the biophysical-signal data set;

rejecting, by the processor, the received biophysical-signal data set based on the comparison; and generating, by the processor, a notification of a failed acquisition of biophysical-signal data set, wherein the notification prompts a subsequent acquisition of the biophysical-signal data set to be performed.

25. The method of claim 24, the at least one template-signal vector data set characteristic of the representative quasi-periodic pattern is determined by:

determining, by the processor, a plurality of signal features characteristically distinct in the received biophysical-signal data set or a portion thereof;

determining, by the processor, a plurality of cycle regions between each of the plurality of determined signal features;

aligning, by the processor, each of the plurality of cycle regions to each other to a same aspect of the plurality of signal features or another set of signal features located in each of the cycle regions; and determining, by the processor, each point of the at least one template-signal vector data set using a mean operation or a median operation performed for each set of points among the plurality of cycle regions.

26. The method of claim 24, wherein the at least one template-signal vector data set characteristic of the representative quasi-periodic pattern is determined by:

performing, by the processor, clustering-based analysis of the plurality of cycle regions to determine presence of more than one dominant cycle morphologies, wherein a template-signal vector is determined for each determined dominant cycle morphology.

27. The method of claim 24 further comprising:

causing, by the processor, transmission of the received biophysical-signal data set over a network to an external analysis system, wherein the analysis system is configured to analyze the received biophysical-signal data for presence, or degree, of a pathology or clinical condition.

28. The method of claim 24, wherein the comparison comprises:

determining presence of asynchronous noise present in the acquired biophysical-signal data set having a value or energy over a pre-defined threshold.

29. A method of quantifying asynchronous noise in an acquired biophysical signal, the method comprising:

receiving, by a processor, a biophysical-signal data set of a subject;

determining, by the processor, a plurality of signal features characteristically distinct in the received biophysical-signal data set or a portion thereof;

determining, by the processor, a plurality of cycle regions between each of the plurality of determined signal features;

aligning, by the processor, each of the plurality of cycle regions to each other to a same aspect of the plurality of signal features or another set of signal features located in each of the cycle regions;

determining, by the processor, each point of the at least one template-signal vector data set using a mean operation or a median operation performed for each set of points among the plurality of cycle regions; and performing, by the processor, clustering-based analysis of the plurality of cycle regions to determine presence of more than one dominant cycle morphologies, wherein a template-signal vector is determined for each determined dominant cycle morphology.

30. A method of rejecting an acquired biophysical signal, the method comprising:
receiving, by a processor, a biophysical-signal data set of a subject;
comparing, by the processor, a received biophysical-signal data set to at least one template-signal vector data set characteristic of a representative quasi-periodic pattern within the biophysical-signal data set; and
rejecting, by the processor, the received biophysical-signal data set based on the comparison,
wherein the at least one template-signal vector data set characteristic of the representative quasi-periodic pattern is determined by:
determining, by the processor, a plurality of signal features characteristically distinct in the received biophysical-signal data set or a portion thereof;
determining, by the processor, a plurality of cycle regions between each of the plurality of determined signal features;
aligning, by the processor, each of the plurality of cycle regions to each other to a same aspect of the plurality of signal features or another set of signal features located in each of the cycle regions; and
determining, by the processor, each point of the at least one template-signal vector data set using a mean operation or a median operation performed for each set of points among the plurality of cycle regions.

31. A method of rejecting an acquired biophysical signal, the method comprising:
receiving, by a processor, a biophysical-signal data set of a subject;
comparing, by the processor, the received biophysical-signal data set to at least one template-signal vector data set characteristic of a representative quasi-periodic pattern within the biophysical-signal data set; and
rejecting, by the processor, the received biophysical-signal data set based on the comparison,
wherein the at least one template-signal vector data set characteristic of the representative quasi-periodic pattern is determined by performing, by the processor, clustering-based analysis of the plurality of cycle regions to determine presence of more than one dominant cycle morphologies, wherein a template-signal vector is determined for each determined dominant cycle morphology.

\* \* \* \* \*